US012735513B2

(12) United States Patent
Yabuuchi et al.

(10) Patent No.: US 12,735,513 B2
(45) Date of Patent: Sep. 15, 2026

(54) HYALURONIC ACID DERIVATIVE, PHARMACEUTICAL COMPOSITION, AND HYALURONIC ACID DERIVATIVE-DRUG COMPLEX

(71) Applicant: ASAHI KASEI KABUSHIKI KAISHA, Tokyo (JP)

(72) Inventors: Kohei Yabuuchi, Tokyo (JP); Yoshiki Miyamoto, Tokyo (JP); Keisuke Fukumoto, Tokyo (JP); Toru Katsumata, Tokyo (JP); Yoshiyuki Nakagawa, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 720 days.

(21) Appl. No.: 17/796,991

(22) PCT Filed: Feb. 4, 2021

(86) PCT No.: PCT/JP2021/004158
§ 371 (c)(1),
(2) Date: Aug. 2, 2022

(87) PCT Pub. No.: WO2021/157665
PCT Pub. Date: Aug. 12, 2021

(65) Prior Publication Data

US 2023/0066990 A1 Mar. 2, 2023

(30) Foreign Application Priority Data

Feb. 7, 2020 (JP) ................................ 2020-019963
Jun. 29, 2020 (JP) ................................ 2020-111674

(51) Int. Cl.
*C08B 37/08* (2006.01)
*A61K 47/36* (2006.01)
*A61K 47/61* (2017.01)
*C07J 9/00* (2006.01)

(52) U.S. Cl.
CPC .......... *C08B 37/0072* (2013.01); *A61K 47/36* (2013.01); *A61K 47/61* (2017.08); *C07J 9/00* (2013.01)

(58) Field of Classification Search
CPC .... C08B 37/0072; A61K 47/36; A61K 47/61; A61K 9/146; A61K 47/60; A61K 38/00; C07J 9/00
See application file for complete search history.

(56) References Cited

U.S. PATENT DOCUMENTS 8,759,322 B2 * 6/2014 Akiyoshi .............. A61K 47/61 536/55.1
2009/0104678 A1 4/2009 Yasuda
2011/0212901 A1 9/2011 Akiyoshi et al.
2015/0032873 A1 1/2015 Chen et al.
2015/0231268 A1 8/2015 Nakai et al.
2019/0142959 A1 5/2019 Nakai et al.
2021/0371548 A1 12/2021 Hattori et al.
2022/0160849 A1 5/2022 Shiku et al.
2023/0085879 A1 3/2023 Nakagawa et al.

FOREIGN PATENT DOCUMENTS

CN 101020724 A 8/2007
CN 103435718 A 12/2013
CN 104603156 A 5/2015
JP H05-058881 A 3/1993
JP 2005-139409 A 6/2005
JP 2007-297542 A 11/2007
JP 2016-500130 A 1/2016
WO 2010/053140 A1 5/2010
WO 2014/038641 A1 3/2014
WO 2017/195880 A1 11/2017
WO 2019/098393 A1 5/2019
WO 2020/158771 A1 8/2020
WO 2021/157677 A1 8/2021

OTHER PUBLICATIONS

Nobbmann, Polydispersity—what does it mean for DLS and chromatography?, website dated Oct. 23, 2017, accessed online at https://www.malvernpanalytical.com/en/learn/knowledge-center/insights/polydispersity-what-does-it-mean-for-dls-and-chromatography on Jan. 14, 2024 (Year: 2017).*
Zhu et al. (RSC Advances, 2017, vol. 7, pp. 23942-23953). (Year: 2017).*
Striegel et al. (Chromatographia, 2018, vol. 81, pp. 823-827) (Year: 2018).*
Gao et al. (The col. 2018, vol. 14, pp. 39-43) (Year: 2018).*
Yokoyama et al., "Analysis of Micelle Formation of an Adriamycin-Conjugated Poly(Ethylene glycol)-Poly(aspartic acid) Block Copolymer by Gel Permeation Chromatography" Pharmaceutical Research vol. 10 No. 6 pp. 895-899 (Year: 1993).*
Gentekos Dillon T et al. "Controlling polymer properties through the shape of the molecular-weight distribution", Nature Reviews Materials, Nature Publishing Group UK, London, vol. 4, No. 12, Oct. 1, 2019 (Oct. 1, 2019), pp. 761-774, XP036954165, DOI: 10.1038/S41578-019-0138-8 [retrieved on Oct. 1, 2019].
He Qingong et al., Polymer materials for oil field development, published by Oil Industry Publishing Co., Ltd. pp. 342-343, Oct. 31, 1990, translation.
Qi-Ye Wu et al., Polymer Rheology, Higher Education Press, pp. 138-142, Oct. 31, 2002, translation.
Ferguson C, Certificate of Analysis, Sodium Hyaluronate 50 kDa, Apr. 16, 2021, p. 1, XP093044323, Retrieved from the Internet: URL:https://echelon-inc.com/wp-content/uploads/2021/05/H-0050_PHI3492P01C_CofA_04162021.pdf [retrieved on May 4, 2023].

(Continued)

*Primary Examiner* — Andrea Olson
(74) *Attorney, Agent, or Firm* — GREENBLUM & BERNSTEIN, P.L.C.

(57) ABSTRACT

The present invention provides a hyaluronic acid derivative having a steryl group introduced therein, wherein a ratio Mw/Mn of a weight-average molecular weight Mw to a number-average molecular weight Mn of the hyaluronic acid derivative is 1.11 or more and 10.0 or less.

10 Claims, 2 Drawing Sheets

(56) References Cited

OTHER PUBLICATIONS

Megan Cooke E et al.: "The rheology of direct and suspended extrusion bioprinting", APL Bioengineering, American Institute of Physics, 2 Huntington Quadrangle, Melville, NY 11747, vol. 5, No. 1, Feb. 4, 2021, XP012253581, DOI: 10.1063/5.0031475 [retrieved on Feb. 4, 2021] p. 11502-1-.

European Search Report issued in EP Patent Application No. 21750644.3, Jun. 15, 2023.

Zhu, Q. et al., "Tumor-Specific Self-Degradable Nanogels as Potential Carriers for Systemic Delivery of Anticancer Proteins", Advanced Functional Materials, vol. 28, 2018, pp. 1707371.

Masuda, Y. et al., "Synthesis of Silica—Hydrophobized Hyaluronic Acid Hybrid Hydrogel", The Chemical Society of Japan, vol. 99th, 2019, pp. 1PB-030; Abstract.

Yamane, S. et al., "Synthesis of hydrophobized hyaluronic acid-calcium phosphate hybrid", The Chemical Society of Japan, vol. 96th, 2016, pp. 2B6-29; Abstract.

ISR issued in International Patent Application No. PCT/JP2021/004158, Apr. 27, 2021, English translation.

Written Opinion issued in International Patent Application No. PCT/JP2021/004158, Apr. 27, 2021, translation.

Measurement of molecular weight distribution of hyaluronic acid by size exclusion chromatography using a low-angle laser light-scattering detector, J. Soc. Cosmet. Chem. Jpn., 1998, 32(2), 147-152, English abstract.

Examination about Viscoelasticity and Molecular Weight Distribution of Hyaluronic Acid, Society of Fiber Science And Technology, Japan Proceedings (Society of Fiber Science And Technology, Japan Proceedings Autumn Research Presentation Meeting), and 2001, 56(3), 151, English translation.

Montanari et al.: "Halting hyaluronidase activity with hyaluronan-based nanohydrogels: development of versatile injectable formulations", Carbohydrate Polymers, vol. 221, Jun. 5, 2019 (Jun. 5, 2019), pp. 209-220, XP085713745, ISSN: 0144-8617, DOI: 10.1016/J.CARBPOL.2019.06.004.

Montanari et al.: "Hyaluronic Acid Nanohydrogels as a Useful Tool for BSAO Immobilization in the Treatment of Melanoma Cancer Cells : Hyaluronic Acid Nanohydrogels as a Useful Tool ?. . . ", Macromolecular Bioscience, vol. 13, No. 9, Jul. 8, 2013 (Jul. 8, 2013), pp. 1185-1194, XP093205062, DE ISSN: 1616-5187, DOI: 10.1002/mabi.201300114 Retrieved from the Internet: URL:https://api.wiley.com/onlinelibrary/tdm/v1/aritcles/10.1002%2Fmabi.201300114.

Anonymous: "Shear thinning—Wikipedia", Mar. 14, 2025, pp. 1-17, XP093259424, Retrieved from the Internet: URL:https://en.m.wikipedia.org/wiki/Shear_thinning.

Morris E R et al.: "Concentration and shear rate dependence of viscosity in random coil polysaccharide solutions", Carbohydrate Polymers, Applied Science Publishers, Ltd Barking, GB, vol. 1, No. 1, Sep. 1, 1981, pp. 5-21, XP024147598, ISSN: 0144-8617, DOI: 10.1016/0144-8617(81)90011-4 [retrieved on Sep. 1, 1981].

* cited by examiner

HYALURONIC ACID DERIVATIVE, PHARMACEUTICAL COMPOSITION, AND HYALURONIC ACID DERIVATIVE-DRUG COMPLEX

TECHNICAL FIELD

The present invention relates to a hyaluronic acid derivative, a pharmaceutical composition, and a hyaluronic acid derivatives-drug complex.

Priority is claimed on Japanese Patent Application No. 2020-019963 filed in Japan on Feb. 7, 2020, and Japanese Patent Application No. 2020-111674 filed in Japan on Jun. 29, 2020, the contents of which are incorporated herein by reference.

BACKGROUND ART

In recent years, biopharmaceuticals, which are pharmaceutical products containing a protein, a peptide or a nucleic acid as an active ingredient, have been put into practical use, and the number thereof is increasing year by year. Biopharmaceuticals can meet unmet medical needs that conventional low-molecular weight drugs could not meet. However, there are problems that they are difficult to be absorbed from the digestive tract or mucous membrane, and are unstable in the body and have a short half-life in blood. Therefore, biopharmaceuticals require frequent administration by injection, which is a heavy burden on both patients and medical personnel. Therefore, there is a demand for a drug substrate (substrate for a sustained-release drug delivery system) that can encapsulate the biopharmaceuticals and gradually release the active ingredient in vivo without impairing pharmacological activity.

In view of such a background, Patent Document 1 and Patent Document 2 propose a substrate for a sustained-release drug delivery system made of a hyaluronic acid derivative having excellent safety. This hyaluronic acid derivative spontaneously associates in an aqueous solution and can efficiently encapsulate a drug, especially biopharmaceuticals, while maintaining its biological activity, and aggregates at physiological salt concentration (or disperses even at physiological salt concentration), and also has a good retainability in blood. Especially, when a biopharmaceutical is used as an active ingredient, this hyaluronic acid derivative can be used as a carrier capable of efficiently encapsulating many drugs while maintaining pharmacological activity, and can be used as a sustained-release carrier in blood and a targeting carrier having an excellent retainability in blood, and also can be used as a local (for example, subcutaneous) sustained-release carrier capable of continuous sustained-release of the drug.

CITATION LIST

Patent Document

[Patent Document 1] PCT International Publication No. WO 2010/053140

[Patent Document 2] Japanese Unexamined Patent Application, First Publication No. 2007-297542

SUMMARY OF INVENTION

Technical Problem

However, the hyaluronic acid derivative described in Patent Document 1 and Patent Document 2 has a problem in that the viscosity is high and the syringeability at the time of injection is not sufficient.

The present invention has been made in view of the above circumstances, and provides a hyaluronic acid derivative having excellent syringeability, a pharmaceutical composition using the hyaluronic acid derivative, and a hyaluronic acid derivative-drug complex.

Solution to Problem

That is, the present invention includes the following aspects.

(1) A hyaluronic acid derivative having a steryl group introduced therein, wherein a ratio Mw/Mn of a weight-average molecular weight Mw to a number-average molecular weight Mn of the hyaluronic acid derivative is 1.11 or more and 10.0 or less.

(2) The hyaluronic acid derivative according to (1), wherein the hyaluronic acid derivative has a weight-average molecular weight of 3,000 or more and 160,000 or less.

(3) The hyaluronic acid derivative according to (1) or (2), wherein the Mw/Mn of the hyaluronic acid derivative is 1.2 or more and less than 3.0.

(4) The hyaluronic acid derivative according to any one of (1) to (3), wherein an introduction rate of the steryl group to the hyaluronic acid derivative is 6% or more and less than 60%.

(5) The hyaluronic acid derivative according to any one of (1) to (4), wherein the hyaluronic acid derivative has a repeating unit represented by the following general formula (I),

[Chemical formula 1]

(I)

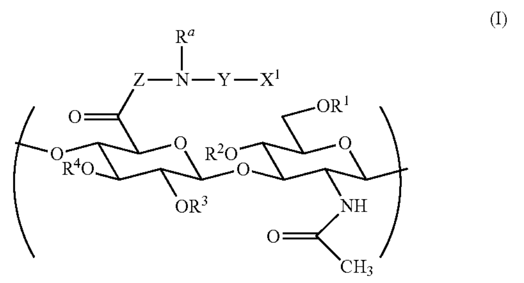

in the formula, $R^1$, $R^2$, $R^3$ and $R^4$ are each independently selected from the group consisting of a hydrogen atom, a $C_{1-6}$ alkyl, a formyl and a $C_{1-6}$ alkyl carbonyl;

Z represents a single bond or a peptide linker having 2 or more and 30 or less amino acid residues;

$X^1$ is a group selected from the group consisting of groups represented by the following formulas:

$-NR^b-R$, $-NR^b-COO-R$, $-NR^b-CO-R$, $-NR^b-CO-NR^c-R$, $-COO-R$, $-O-COO-R$, $-S-R$, $-CO-Y^a-S-R$,

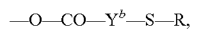
$—O—CO—Y^b—S—R$,

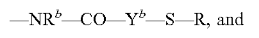
$—NR^b—CO—Y^b—S—R$, and

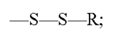
$—S—S—R$;

$R^a$, $R^b$ and $R^c$ are each independently selected from the group consisting of a hydrogen atom, a $C_{1-20}$ alkyl, an amino $C_{2-20}$ alkyl and a hydroxy $C_{2-20}$ alkyl, where an alkyl moiety of the groups may be inserted with a group selected from the group consisting of —O— and $—NR^f—$;

$R^f$ is selected from the group consisting of a hydrogen atom, a $C_{1-12}$ alkyl, an amino $C_{2-12}$ alkyl and a hydroxy $C_{2-12}$ alkyl, and an alkyl moiety of the groups may be inserted with a group selected from the group consisting of —O— and —NH—;

R is a steryl group;

Y is a $C_{2-30}$ alkylene or $—(CH_2CH_2O)_m—CH_2CH_2—$, where the alkylene may be inserted with a group selected from the group consisting of —O—, $—NR^g$- and —S—S—;

$R^g$ is selected from the group consisting of a hydrogen atom, a $C_{1-20}$ alkyl, an amino $C_{2-20}$ alkyl and a hydroxy $C_{2-20}$ alkyl, and an alkyl moiety of the groups may be inserted with a group selected from the group consisting of —O— and —NH—;

$Y^a$ is a $C_{1-5}$ alkylene;

$Y^b$ is a $C_{2-8}$ alkylene or a $C_{2-8}$ alkenylene;

m is an integer of 1 or more and 100 or less.

(6) The hyaluronic acid derivative according to (5), wherein R is a cholesteryl group.

(7) The hyaluronic acid derivative according to any one of (1) to (6), wherein the ratio Mw/Mn of the weight-average molecular weight Mw to the number-average molecular weight Mn of the hyaluronic acid derivative is 1.2 or more and 2.9 or less.

(8) The hyaluronic acid derivative according to any one of (1) to (7), wherein the hyaluronic acid derivative has a weight-average molecular weight of 7,000 or more and 120,000 or less.

(9) A pharmaceutical composition comprising the hyaluronic acid derivative according to any one of (1) to (8) as a carrier.

(10) The pharmaceutical composition according to (9), wherein a drug forms a complex with the hyaluronic acid derivative.

(11) The pharmaceutical composition according to (9) or (10), wherein the drug is a protein, a peptide or a nucleic acid having pharmacological activity.

(12) A hyaluronic acid derivative-drug complex in which one or more drugs are complexed with the hyaluronic acid derivative according to any one of (1) to (8).

Advantageous Effects of Invention

According to the hyaluronic acid derivatives of the above aspects, it is possible to provide a hyaluronic acid derivative having excellent syringeability.

DESCRIPTION OF EMBODIMENTS

Figure 1:
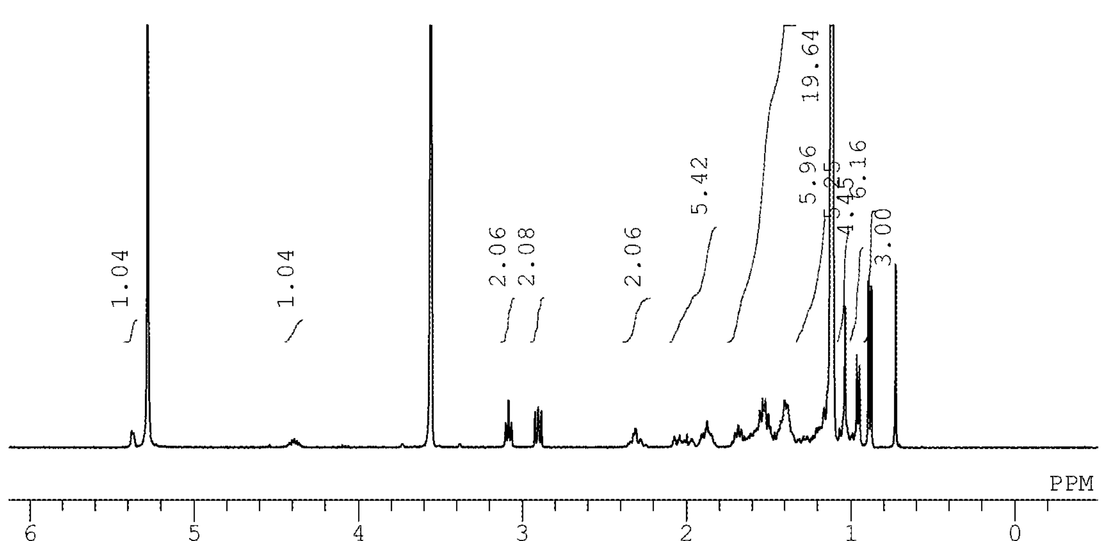
FIG. 1 is a $^1$H-NMRspectrum of cholesteryl 6-aminohexyl carbamate hydrochloride in Example 1.

Hereinafter, embodiments of the present invention (hereinafter referred to as "the present embodiment") will be described in detail, but the present invention is not limited thereto, and various modifications can be made within the scope of the present embodiment.

Hereinafter, the terms used in the present description will be described.

As used herein, the term "$C_{1-20}$ alkyl" means a linear or branched alkyl group having 1 or more and 20 or less carbon atoms, and examples thereof include a "$C_{1-4}$ alkyl" such as a methyl, ethyl, n-propyl, iso-propyl, n-butyl, sec-butyl, iso-butyl, tert-butyl or the like, an n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, 2-ethylbutyl, and the like. The $C_{1-20}$ alkyl also includes a C1-12 alkyl having 1 or more and 12 or less carbon atoms, and a C1-6 alkyl group having 1 or more and 6 or less carbon atoms.

As used herein, the term "$C_{1-6}$ alkyl carbonyl" means an alkyl carbonyl group whose alkyl moiety is the $C_{1-6}$ alkyl already mentioned above, and examples thereof include a "$C_{1-4}$ alkyl carbonyl" such as an acetyl, propionyl, n-propylcarbonyl, iso-propylcarbonyl, n-butylcarbonyl, sec-butylcarbonyl, iso-butylcarbonyl, tert-butylcarbonyl or the like, and the like.

As used herein, the term "amino $C_{2-20}$ alkyl" means a linear or branched alkyl having 2 or more and 20 or less carbon atoms and having an amino group as a substituent, for example, the amino group may be located on the carbon atom at the terminal of the alkyl group. Examples of the amino $C_{2-20}$ alkyl also include an amino $C_{2-12}$ alkyl having 2 or more and 12 or less carbon atoms.

As used herein, the term "hydroxy $C_{2-20}$ alkyl" means a linear or branched alkyl group having 2 or more and 20 or less carbon atoms and having a hydroxyl group as a substituent, for example, the hydroxyl group may be located on the carbon atom at the terminal of the alkyl group. Examples of the hydroxy $C_{2-20}$ alkyl also include a hydroxy $C_{2-12}$ alkyl having 2 or more and 12 or less carbon atoms.

As used herein, the term "$C_{2-30}$ alkylene" means a linear or branched divalent saturated hydrocarbon group having 2 to 30 carbon atoms, such as an ethylene, propylene or the like, and examples thereof also include a $C_{2-20}$ alkylene having 2 or more and 20 or less carbon atoms, a $C_{2-8}$ alkylene having 2 or more and 8 or less carbon atoms, and a group "$—(CH_2)_n—$" (where n is 2 or more and 30 or less, preferably 2 or more and 20 or less, and more preferably 2 or more and 15 or less).

As used herein, the term "$C_{1-5}$ alkylene" means a linear or branched divalent saturated hydrocarbon group having 1 or more and 5 or less carbon atoms, and examples thereof include a methylene, ethylene, propylene and the like.

As used herein, the term "$C_{2-8}$ alkenylene" means a linear or branched divalent saturated hydrocarbon group containing one or more double bonds and having 2 or more and 8 or less carbon atoms, and examples thereof include-CH═CH—, $—C(CH_3)═CH—$, 2-butene-1,4-diyl, hepta-2,4-diene-1,6-diyl, octa-2,4,6-triene-1,8-diyl and the like. If geometric isomers exist, the isomers and mixtures thereof are also included.

<<Hyaluronic Acid Derivative>>

The hyaluronic acid derivative of the present embodiment is a hyaluronic acid derivative having a steryl group introduced therein. The ratio Mw/Mn of the weight-average molecular weight Mw to the number-average molecular weight Mn of the hyaluronic acid derivative of the present embodiment (hereinafter, may be referred to as "polydispersity") is 1.11 or more and 10.0 or less.

Since the hyaluronic acid derivative of the present embodiment has a polydispersity within the above range, it has an excellent ability to reduce the viscosity in response to the shear at the time of injection, and provides good syringeability. In particular, when the degree of polydispersity of the hyaluronic acid derivative is at least the above lower limit, entanglement between the molecules when a shear is applied can be relaxed, and the syringeability is improved.

[Mw/Mn(Polydispersity)]

The Mw/Mn (polydispersity) is 1.11 or more and 10.0 or less, preferably 1.2 or more and less than 3.0, more preferably 1.2 or more and 2.9 or less, even more preferably 1.3 or more and 2.9 or less, still even more preferably 1.3 or more and 2.4 or less, still even more preferably 1.3 or more and 2.1 or less, and still even more preferably 1.5 or more and 2.1 or less.

When Mw/Mn is equal to or higher than the above lower limit, the shear-thinning property of the hyaluronic acid derivative can be induced, and the viscosity can be lowered in response to the shear at the time of injection, thereby improving the syringeability. When Mw/Mn is equal to or higher than the above lower limit, the proportion of low-molecular-weight hyaluronic acids increases, but since the number of modifying groups bonded to one molecule of hyaluronic acid decreases in the low-molecular-weight hyaluronic acid, the hydrophobic interaction between the molecules becomes weak. Therefore, it is presumed that the viscosity decreases largely when the shearing force is applied, and the difference between when the shearing force is weak and when the shearing force is strong becomes larger. When Mw/Mn is less than (or not higher than) the above upper limit, it is possible to suppress a decrease in the local retainability of the hyaluronic acid derivative in the living body. The term "shear-thinning property" as used herein means a property in which the viscosity decreases as the shear rate increases.

Mw/Mn (polydispersity) can be calculated from, for example, the weight-average molecular weight Mw and the number-average molecular weight Mn determined by a size exclusion chromatography multi-angle light scattering detector (SEC-MALS). Specifically, Mw/Mn (polydispersity) can be measured according to the method described later in the Examples.

[Weight-Average Molecular Weight Mw]

Although the weight-average molecular weight Mw of the hyaluronic acid derivative is not particularly limited, a hyaluronic acid derivative having a relatively large molecular weight is preferable from the viewpoint of expecting a sustained-release function derived from a diffusion-delay in local administration, and when the final dosage form is a solution preparation, a hyaluronic acid derivative having a relatively low-molecular-weight is preferable from the viewpoint of syringeability. Therefore, the weight-average molecular weight Mw of the hyaluronic acid derivative is preferably 3,000 (3 kDa) or more and 160,000 (160 kDa) or less, more preferably 7,000 (7 kDa) or more and 160,000 (160 kDa) or less, even more preferably 7,000 (7 kDa) or more and 120,000 (120 kDa) or less, still even more preferably 7 kDa or more and 60 kDa or less, and most preferably 10 kDa or more and 50 kDa or less.

Generally, the weight-average molecular weight Mw and the number-average molecular weight Mn of the hyaluronic acid derivative can be adjusted by using a raw material having a corresponding molecular weight. Furthermore, it is also possible to control the molecular weight by adding a cross-linking agent or conducting intermolecular cross-linking.

The weight-average molecular weight Mw and the number-average molecular weight Mn of the hyaluronic acid derivative can be measured by, for example, a size exclusion chromatography multi-angle light scattering detector (SEC-MALS). The weight-average molecular weight Mw and the number-average molecular weight Mn of the hyaluronic acid derivative can be specifically measured according to the method described later in the Examples.

[Steryl Group]

In the hyaluronic acid derivative, the steryl group may be directly bonded to a hyaluronic acid, or may be bonded through a linker.

As the "linker" here, any peptide linker or synthetic compound linker that can be introduced by genetic engineering may be used, and in the hyaluronic acid derivative, a peptide linker is preferable. Although the length of the peptide linker is not particularly limited, and can be appropriately selected by those skilled in the art depending on the intended purpose, the length is preferably 2 amino acids or more (the upper limit is not particularly limited, but usually 30 amino acids or less, preferably 20 amino acids or less), and particularly preferably 15 amino acids. As the peptide linkers contained in the hyaluronic acid derivative, peptide linkers having the same length may be used, or peptide linkers having different lengths may be used.

The term "steryl group" as used herein is not particularly limited as long as it is a group having a steroid skeleton. Here, specific examples of the steroid include a cholesterol, cholestanol, campestanol, ergostanol, stigmastanol, coprostanol, stigmasterol, sitosterol, lanosterol, ergosterol, simiarenol, bile acid, testosterone, estradiol, progesterone, cortisol, cortisone, aldosterone, corticosterone, deoxycortisterone and the like. Examples of the steryl group include a cholesteryl group, a stigmasteryl group, a lanosteryl group, an ergosteryl group and the like, and among them, a cholesteryl group (particularly, a cholester-5-en-3β-yl group) is preferable.

[Steryl Group Introduction Rate]

The introduction rate of steryl groups to the hyaluronic acid derivative (hereinafter, may be simply referred to as "steryl group introduction rate") is preferably 6% or more and less than 60%, more preferably 6% or more and 50% or less, even more preferably 6% or more and 40% or less, particularly preferably 6% or more and 35% or less, and most preferably 8% or more and 22% or less.

When the steryl group introduction rate is within the above range, the hyaluronic acid derivative can dissolve well in pure water or under a low salt concentration, have shear-thinning property, and be imparted with syringeability. Further, by complexing a hyaluronic acid derivative having a steryl group introduction rate within the above range with a drug, and administering it into the body (for example, subcutaneous administration), a long-term sustained-release preparation staying at the administration site can be obtained.

Further, from the viewpoint of improving the local retainability at the administration site described above, the steryl group introduction rate is preferably 6% or more and less than 35%, more preferably 8% or more and 33% or less, and even more preferably 12% or more and 22% or less. On the other hand, from the viewpoint of stable dispersion by suppressing the drug-aggregation, the steryl group introduction rate is preferably 35% or more and less than 60%, and more preferably 35% or more and 50% or less.

The steryl group introduction rate can be measured by $^1$H-NMRmeasurement. That is, it can be calculated based on the following formula using the integral value of the peak derived from the steryl groups of the hyaluronic acid derivative in $^1$H-NMRspectrum and the integral value of the peak derived from the acetyl groups of N-acetyl-D-glucosamine contained in the hyaluronic acid derivative ($COCH_3$, 1.6 ppm or more and 2.0 ppm or less, 3H). In the formula, nH represents the number of hydrogen atoms corresponding to the peak. Specifically, for example, the measurement can be performed according to the method described later in the Examples.

[Steryl group introduction rate](%)=[(Peak integrated value derived from steryl group×3/$n_H$)/(Peak integrated value derived from acetyl group of N-acetyl-D-glucosamine)]×100

Specific examples of the preferred hyaluronic acid derivative include hyaluronic acid derivatives having one or more repeating units represented by the following general formula (I) (hereinafter, may be referred to as "repeating unit (I)").

[Chemical formula 2]

(I)

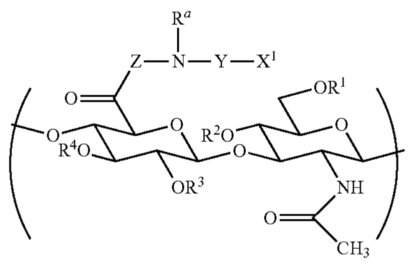

(In the formula, $R^1$, $R^2$, $R^3$ and $R^4$ are each independently selected from the group consisting of a hydrogen atom, a $C_{1-6}$ alkyl, a formyl and a $C_{1-6}$ alkyl carbonyl;

Z represents a single bond or a peptide linker having 2 or more and 30 or less amino acid residues;

$X^1$ is a group selected from the group consisting of groups represented by the following formulas:

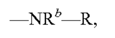

$—NR^b—R$,

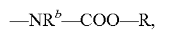

$—NR^b—COO—R$,

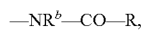

$—NR^b—CO—R$,

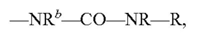

$—NR^b—CO—NR—R$,

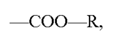

—COO—R,

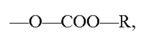

—O—COO—R,

—S—R,

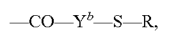

$—CO—Y^b—S—R$,

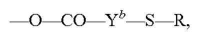

$—O—CO—Y^b—S—R$,

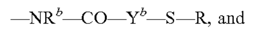

$—NR^b—CO—Y^b—S—R$, and

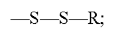

—S—S—R;

$R^a$, $R^b$ and $R^c$ are each independently selected from the group consisting of a hydrogen atom, a $C_{1-20}$ alkyl, an amino $C_{2-20}$ alkyl and a hydroxy $C_{2-20}$ alkyl, where an alkyl moiety of the groups may be inserted with a group selected from the group consisting of —O— and $—NR^f—$;

$R^f$ is selected from the group consisting of a hydrogen atom, a $C_{1-12}$ alkyl, an amino $C_{2-12}$ alkyl and a hydroxy $C_{2-12}$ alkyl, and an alkyl moiety of the groups may be inserted with a group selected from the group consisting of —O— and —NH—;

R is a steryl group;

Y is a $C_{2-30}$ alkylene or $—(CH_2CH_2O)_m—CH_2CH_2—$, where the alkylene may be inserted with a group selected from the group consisting of —O—, —NR— and —S—S—;

$R^g$ is selected from the group consisting of a hydrogen atom, a $C_{1-20}$ alkyl, an amino $C_{2-20}$ alkyl and a hydroxy $C_{2-20}$ alkyl, and an alkyl moiety of the groups may be inserted with a group selected from the group consisting of —O— and —NH—;

$Y^a$ is a $C_{1-5}$ alkylene;

$Y^b$ is a $C_{2-8}$ alkylene or a $C_{2-8}$ alkenylene;

m is an integer of 1 or more and 100 or less.)

The hyaluronic acid derivative is preferably a hyaluronic acid derivative having one or more repeating units represented by the following general formula (Ia) (hereinafter, may be referred to as "repeating unit (Ia)").

[Chemical formula 3]

(Ia)

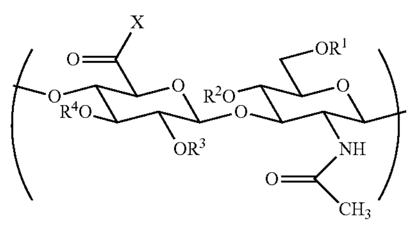

(In the formula, $R^1$, $R^2$, $R^3$ and $R^4$ are each independently selected from the group consisting of a hydrogen atom, a $C_{1-6}$ alkyl, a formyl and a $C_{1-6}$ alkyl carbonyl;

X is a hydrophobic group represented by $—NR^a—Y—NR^b—COO—R$;

$R^a$ and $R^b$ are each independently selected from the group consisting of a hydrogen atom and a $C_{1-6}$ alkyl;

R is a steryl group;

Y is a $C_{2-30}$ alkylene or $—(CH_2CH_2O)_m—CH_2CH_2—$, m is an integer of 1 or more and 100 or less.)

Here, when the hyaluronic acid derivative has two or more repeating units (I) or repeating units (Ta), the repeating units may be the same or different.

The hyaluronic acid derivative may be modified at positions other than the repeating unit (I) or repeating unit (Ta), and for example, the hydroxyl group may be converted to $—O(C_{1-6}$ alkyl), —O(formyl), $—O(C_{1-6}$ alkylcarbonyl) or the like, and the carboxyl group may be converted to an amide or an ester, or may form a salt.

[Repeating Unit (I)]

The group "—Z—N($R^a$)—Y—$X^1$" in the general formula (I) may be a group selected from the group consisting of the groups represented by the following formulas:

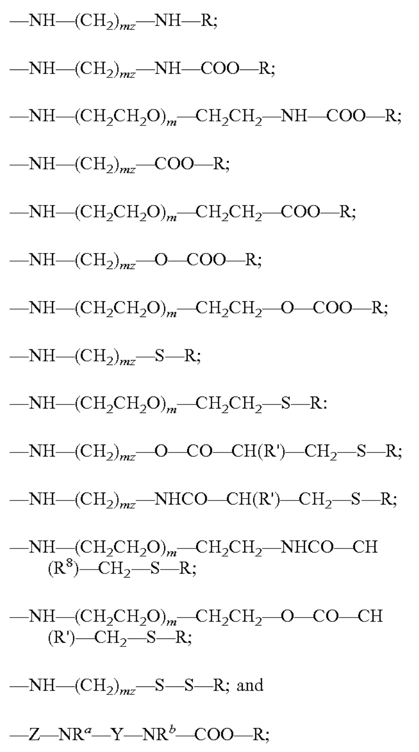

—NH—$(CH_2)_{mz}$—NH—R;

—NH—$(CH_2)_{mz}$—NH—COO—R;

—NH—$(CH_2CH_2O)_m$—$CH_2CH_2$—NH—COO—R;

—NH—$(CH_2)_{mz}$—COO—R;

—NH—$(CH_2CH_2O)_m$—$CH_2CH_2$—COO—R;

—NH—$(CH_2)_{mz}$—O—COO—R;

—NH—$(CH_2CH_2O)_m$—$CH_2CH_2$—O—COO—R;

—NH—$(CH_2)_{mz}$—S—R;

—NH—$(CH_2CH_2O)_m$—$CH_2CH_2$—S—R:

—NH—$(CH_2)_{mz}$—O—CO—CH(R')—$CH_2$—S—R;

—NH—$(CH_2)_{mz}$—NHCO—CH(R')—$CH_2$—S—R;

—NH—$(CH_2CH_2O)_m$—$CH_2CH_2$—NHCO—CH($R^8$)—$CH_2$—S—R;

—NH—$(CH_2CH_2O)_m$—$CH_2CH_2$—O—CO—CH(R')—$CH_2$—S—R;

—NH—$(CH_2)_{mz}$—S—S—R; and

—Z—$NR^a$—Y—$NR^b$—COO—R;

(Here, mz is an integer of 2 or more and 30 or less, $R^8$ is a hydrogen atom or a methyl group, and R and m are as already defined in the present description.)

This group is preferably a group selected from

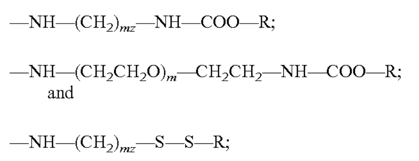

—NH—$(CH_2)_{mz}$—NH—COO—R;

—NH—$(CH_2CH_2O)_m$—$CH_2CH_2$—NH—COO—R; and

—NH—$(CH_2)_{mz}$—S—S—R;

(Here, mz, R and m are as already defined in the present description.)

(Z)

In the general formula (I), Z is preferably a single bond. Further, in another embodiment, when Z is a peptide linker, $X^1$ is preferably —$NR^b$—COO—R. Further, in another embodiment, Z may be a peptide linker represented by —NH—[CH(—$Z^a$)—CONH$]_{n-1}$—CH(—$Z^a$)—CO—, and here, n is an integer of 2 or more and 30 or less, and $Z^a$ each independently represents a substituent in the α-amino acid represented by $H_2N$—CH(—$Z^a$)—COOH. The peptide linker bonds to the carboxyl group of the glucuronic acid moiety at the N-terminal and bonds to the group-N(—$R^a$)—Y—$X^1$ at the C-terminal. As the amino acids that can be used as the amino acid residues of the peptide linker, α-amino acids, for example, natural (L-type) amino acids such as alanine, arginine, asparagine (Asn), aspartic acid, cysteine, glutamine, glutamic acid, glycine (Gly), histidine, isoleucine, leucine (Leu), lysine, methionine, phenylalanine (Phe), proline, serine, threonine, tryptophan, tyrosine, valine, D-type thereof, and the like can be mentioned, and all α-amino acids, including synthesized amino acids, can be used. That is, examples of $Z^a$ include-$CH_3$, $H_2NC(NH)NH(CH_2)_3$—, $H_2NCOCH_2$- and the like. Further, the n Zs may be the same or different. n is an integer of 2 or more and 30 or less, preferably 2 or more and 10 or less, and more preferably 2 or more and 4 or less. Preferred examples of the peptide linker include, for example, -Gly-Phe-Leu-Gly-, -Asn-Phe-Phe-, -Phe-Phe-, Phe-Gly- and the like.

(Y)

In the general formula (I), Y is preferably selected from the group consisting of —$(CH_2)_{n1}$- and —$(CH_2CH_2O)_{m1}$—$CH_2CH_2$-(where n1 is an integer of 2 or more and 20 or less, preferably an integer of 2 or more and 15 or less, more preferably an integer of 2 or more and 12 or less, and even more preferably an integer of 2 or more and 6 or less, m1 is an integer of 1 or more and 4 or less). Specifically, —$(CH_2)_2$—, —$(CH_2)_6$—, —$(CH_2)_8$—, —$(CH_2)_{12}$—, or —$(CH_2CH_2O)_2$—$CH_2CH_2$— is preferable. Further, from the viewpoint of achieving high solubility in pure water or at a low salt concentration and exhibiting high precipitation forming ability at physiological salt concentration, Y is preferably selected from the group consisting of —$(CH_2)_2$—, —$(CH_2)_6$—, —$(CH_2)_8$— and —$(CH_2)_{12}$, and more preferably —$(CH_2)_6$.

Y may also be, for example, —$CH_2CH_2O$—$CH_2CH_2$—S—S—$CH_2CH_2O$—$CH_2CH_2$—, —$(CH_2CH_2O)_2$—$CH_2CH_2$—S—S—$CH_2CH_2O$—$CH_2CH_2$—, —$CH_2CH_2O$—$CH_2CH_2$—S—S—$(CH_2CH_2O)_2$—$CH_2CH_2$—, —$(CH_2CH_2O)_2$—$CH_2CH_2$—S—S—$(CH_2CH_2O)_2$—$CH_2CH_2$— or the like.

($Y^a$)

$Y^a$ is preferably —$CH_2$— or —$CH_2$—$CH_2$—.

($Y^b$)

$Y^b$ is preferably-$CH_2$—$CH_2$—, —$CH(CH_3)CH_2$—, 2-butene-1,4-diyl, hepta-2,4-diene-1,6-diyl or octa-2,4,6-triene-1,8-diene, and more preferably-$CH_2$—$CH_2$— or —$CH(CH_3)CH_2$—.

Examples of the group "—Z—N($R^a$)Y—$X^1$" include-NH—$(CH_2)_2$—NH—CO-cholesteryl, —NH—$(CH_2)_4$—NH—$(CH_2)_3$—NH—$(CH_2)_3$—NH—COO-cholesteryl, —NH—$(CH_2)_3$—NH—$(CH_2)_4$—NH—$(CH_2)_3$—NH—COO-cholesteryl, —NH—$(CH_2)_4$—NH—$(CH_2)_3$—NH—COO-cholesteryl, —NH—$(CH_2)_4$—N(—$(CH_2)_3$—$NH_2$)—COO-cholesteryl, —NH—$(CH_2)_3$—NH—$(CH_2)_4$—N(—$(CH_2)_3$—$NH_2$)—COO-cholesteryl, —NH—$(CH_2)_3$—NH—$(CH_2)_4$—N(—$(CH_2)_3$—NH—$(CH_2)_3$—$NH_2$)—COO-cholesteryl, —NH—$(CH_2)_3$—NH—$(CH_2)_4$—N(—$(CH_2)_3$—$NH_2$)—CO—NH-cholesteryl, —NH—$(CH_2)_3$—NH—$(CH_2)_4$—N(—$(CH_2)_3$—$NH_2$)—CO-cholesteryl, —NH—$(CH_2)_3$—NH—$(CH_2)_4$—N(—$(CH_2)_3$—$NH_2$)-cholesteryl and the like. Of these, a group "—Z—N($R^a$)Y—$X^1$", wherein $R^a$, $R^b$ and $R^C$ are hydrogen atoms, Y is a linear $C_{2-30}$ alkylene or —$(CH_2CH_2O)_m$—$CH_2CH_2$—, $Y^a$ is a linear $C_{1-5}$ alkylene, and $Y^b$ is a linear $C_{2-8}$ alkylene or linear $C_{2-8}$ alkenylene, is preferable.

[Repeating Unit (Ta)]

In the general formula (Ia), X preferably is-NH—$(CH_2)_2$—NH—COO-cholesteryl, —NH—$(CH_2)_6$—NH—COO-cholesteryl, —NH—$(CH_2)_{12}$—NH—COO-cholesteryl or —NH—$(CH_2CH_2O)_2$—$CH_2CH_2$—NH—COO-cholesteryl, and more preferably-NH—$(CH_2)_2$—NH—COO-cholesteryl, —NH—$(CH_2)_6$—NH—COO-cholesteryl or —NH—$(CH_2CH_2O)_2$—$CH_2CH_2$—NH—COO-cholesteryl.

The hyaluronic acid derivative may further contain a repeating unit represented by the general formula (II) (hereinafter, may be referred to as "repeating unit (II)") in addition to the repeating unit (I).

[Chemical formula 4]

(II)

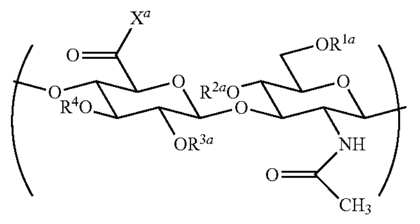

(In the formula, $R^{1a}$, $R^{2a}$, $R^{3a}$, and $R^{4a}$ are each independently selected from the group consisting of a hydrogen atom, a $C_{1-6}$ alkyl, a formyl and a $C_{1-6}$ alkyl carbonyl;

$X^a$ is selected from the group consisting of a hydroxy and —O-$Q^+$; where $Q^+$ is a counter cation.)

Here, when the hyaluronic acid derivative contains two or more repeating units (II), the repeating units may be the same or different.

In another embodiment, the hyaluronic acid derivative may be a hyaluronic acid derivative substantially containing the repeating unit (I), the repeating unit (Ia) and the repeating unit (II).

[Repeating Unit (II)]

In the general formula (II), $Q^+$ is not particularly limited as long as it is a counter cation that forms a salt with a carboxyl group in water, and if it is divalent or higher, it forms a salt with a plurality of carboxyl groups according to the valence number. Examples of the counter cation include metal ions such as a lithium ion, sodium ion, rubidium ion, cesium ion, magnesium ion, calcium ion; ammonium ions represented by formula: $N^+R^jR^kR^lR^m$ (in the formula, $R^j$, $R^k$, $R^l$ and $R^m$ are each independently selected from the group consisting of a hydrogen atom and a $C_{1-6}$ alkyl). Among them, $Q^+$ is preferably a sodium ion, potassium ion, or a tetraalkylammonium ion (for example, a tetra n-butylammonium ion or the like). $R^j$, $R^k$, $R^l$ and $R^m$ are preferably the same group selected from the group consisting of a $C_{1-6}$ alkyl, and more preferably an n-butyl group.

It is preferable that $R^1$, $R^2$, $R^3$ and $R^4$, and $R^{1a}$, $R^{2a}$, $R^{3a}$, and $R^{4a}$ all be hydrogen atoms. Further, it is preferable that both $R^a$ and $R^b$ be hydrogen atoms.

Of these, the hyaluronic acid derivative is preferably a hyaluronic acid derivative substantially containing the repeating unit (I) and the repeating unit (II). In the hyaluronic acid derivative, for example, 80% or more, preferably 90% or more, even more preferably 95% or more of the repeating units of the disaccharide composed of D-glucuronic acid and N-acetyl-D-glucosamine contained in the derivative are the repeating unit (I) and the repeating unit (II). The hyaluronic acid derivative may be composed of only the repeating unit (I) and the repeating unit (II).

<Manufacturing Method of Hyaluronic Acid Derivative>

The hyaluronic acid derivative of the present embodiment can be obtained, for example, by converting the carboxyl group of glucuronic acid into an amide and introducing a steryl group. Further, the steryl group introduction rate can be set to 6% or more and less than 60% by adjusting the blending amount of the compound having a steryl group to be reacted with a hyaluronic acid or derivative thereof as a raw material.

Specific examples of the method for converting the carboxyl group of glucuronic acid into an amide to introduce a steryl group include, for example, a method in which a raw material hyaluronic acid or derivative thereof, preferably a hyaluronic acid or derivative thereof composed of only the repeating unit (II), is ion-exchanged with a tetraalkylammonium salt (for example, a tetrabutylammonium (TBA) salt), and in the presence of a suitable condensing agent, the hyaluronate and a steryl group (particularly, a cholesteryl group) represented by formula: $HNR^a$—Y—$NR^b$—R, $NHR^a$—Y—$NR^b$—COO—R, $HNR^a$—Y—$NR^b$—COO—R, $HNR^a$—Y—$NR^b$—CO—R, $HNR^a$—Y—$NR^b$—CO—$NR^c$—R, $HNR^a$—Y—COO—R, $HNR^a$—Y—O—COO—R, $HNR^a$—Y—S—R, $HNR^a$—Y—CO—$Y^a$—S—R, $HNR^a$—Y—O—CO—$Y^b$—S—R, $HNR^a$—Y—$NR^b$—CO—$Y^b$—S—R, $HNR^a$—Y—S—S—R, or —Z—$NR^a$—Y—$NR^b$—COO—R (in the formulas, $R^a$, $R^b$, Re, Y, $Y^a$, $Y^b$, Z and R are as already defined in the present description), are reacted in a solvent.

The condensing agent that can be used in the above reaction is not particularly limited, and examples thereof include 4-(4,6-dimethoxy-1,3,5-triazine)-4-methylmorpholium (DMT-MM), N,N'-carbonyldiimidazole (CDI), N,N'-dicyclohexylcarbodiimide (DCC), N-ethoxycarbonyl-2-ethoxy-1,2-dihydroquinoline (EEDQ), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazole-1-oxy-tris-pyrrolidino-phosphonium hexafluorophosphate (PyBOP), benzotriazole-1-yl-oxy-tris (dimethylamino) phosphonium hexafluorophosphate (BOP), 1-ethyl-3-(3-dimethylaminopropyl) carbodiimide (EDC), N-hydroxysuccinimide (NHS) and the like.

Although it is not particularly limited, DMT-MM is preferable from the viewpoint that the reaction proceeds with high efficiency even in a mixed solvent of water and an organic solvent. Further, by using DMT-MM as a condensing agent, it is possible to highly selectively form an amide bond by an amino group and a carboxyl group while suppressing the formation of an ester bond in a system in which a large number of hydroxyl groups coexist. By using this condensing agent, for example, alcohol as a solvent reacts with the carboxyl group of the hyaluronic acid moiety, or the carboxyl group and hydroxyl group simultaneously present in the hyaluronic acid moiety are bonded intramolecularly or intermolecularly, thereby making it possible to prevent the formation of unwanted cross-links.

Examples of the solvent used in the steryl group introduction reaction include water, DMSO, methanol, ethanol, propanol, butanol, isopropanol, polyhydric alcohol, acetonitrile, DMF, THF, dichloromethane, chloroform, hexane, diethyl ether, ethyl acetate, a mixture thereof, and the like. Examples of the polyhydric alcohol include those similar to those exemplified in the above-mentioned "(B) alcohol", and among them, an ethylene glycol is preferable.

Alternatively, a method in which a raw material hyaluronic acid or derivative thereof is ion-exchanged with a tetraalkylammonium salt (for example, a tetrabutylammonium (TBA) salt), the hyaluronate and the spacer moiety are reacted in a solvent in the presence of a suitable condensing agent (at this time, a protection and deprotection reaction may be carried out if necessary) to convert the carboxyl group (—COOH) of the raw material hyaluronic acid or derivative thereof, followed by reacting with a suitable reagent, may also be used. Examples of the combination of the group derived from the carboxyl group and the reaction reagent are shown below.

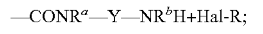

—$CONR^a$—Y—$NR^b$H+Hal-R;

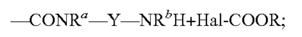

—$CONR^a$—Y—$NR^b$H+Hal-COOR;

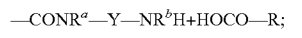

—$CONR^a$—Y—$NR^b$H+HOCO—R;

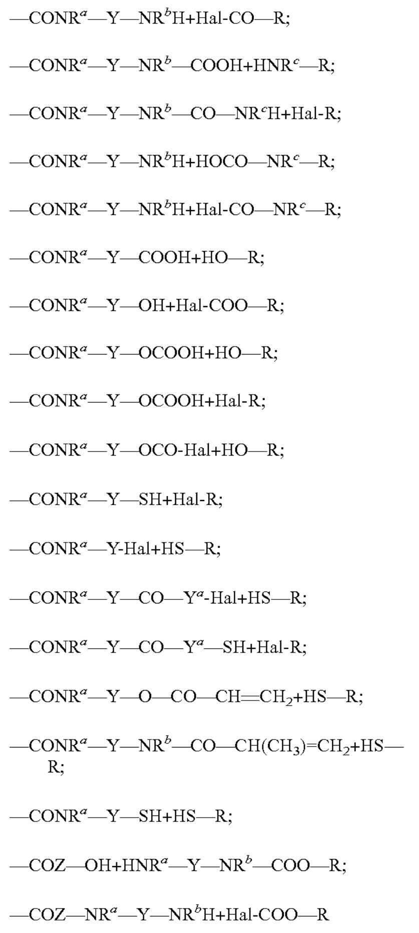

—CONR$^a$—Y—NR$^b$H+Hal-CO—R;

—CONR$^a$—Y—NR$^b$—COOH+HNR$^c$—R;

—CONR$^a$—Y—NR$^b$—CO—NR$^c$H+Hal-R;

—CONR$^a$—Y—NR$^b$H+HOCO—NR$^c$—R;

—CONR$^a$—Y—NR$^b$H+Hal-CO—NR$^c$—R;

—CONR$^a$—Y—COOH+HO—R;

—CONR$^a$—Y—OH+Hal-COO—R;

—CONR$^a$—Y—OCOOH+HO—R;

—CONR$^a$—Y—OCOOH+Hal-R;

—CONR$^a$—Y—OCO-Hal+HO—R;

—CONR$^a$—Y—SH+Hal-R;

—CONR$^a$—Y-Hal+HS—R;

—CONR$^a$—Y—CO—Y$^a$-Hal+HS—R;

—CONR$^a$—Y—CO—Y$^a$—SH+Hal-R;

—CONR$^a$—Y—O—CO—CH═CH$_2$+HS—R;

—CONR$^a$—Y—NR$^b$—CO—CH(CH$_3$)=CH$_2$+HS—R;

—CONR$^a$—Y—SH+HS—R;

—COZ—OH+HNR$^a$—Y—NR$^b$—COO—R;

—COZ—NR$^a$—Y—NR$^b$H+Hal-COO—R (In the formula, R$^a$, R$^b$, R$^c$, Y, Ya, Y$^b$ and Z are as already defined in the present description, and Hal represents a halogen atom selected from the group consisting of a fluorine atom, a chlorine atom, a bromine atom, and an iodine.)

Examples of the reaction patterns include a dehydrohalogenation reaction, a condensation reaction, a dehydration reaction, a nucleophilic addition reaction such as Michael addition or the like, an oxidative disulfide formation reaction, and the like. These are well-known reactions and can be carried out by those skilled in the art by appropriately selecting and finding favorable reaction conditions. When the converter or the reactant has a carboxyl group, an N-hydroxysuccinimide (hereinafter, also referred to as "NHS") ester may be used in the reaction.

Further, a method in which a 2-aminoethyl 2-pyridyl disulfide is reacted with the carboxyl group of the raw material hyaluronic acid or derivative thereof to prepare a hyaluronic acid derivative into which a spacer having a mercapto group modified with a leaving group is introduced at the terminal, followed by forming a disulfide bond by subjecting it to a nucleophilic substitution reaction with thiocholesterol, may be mentioned.

Further, there is also a method of preparing a hyaluronic acid or derivative thereof in which some of the spacers are introduced into the carboxyl group and preparing a steryl group in which some of the spacers are introduced, followed by reacting them. Although some specific examples have been described above, when —S—S— is inserted into Y, there is also a method of preparing a hyaluronic acid derivative in which a spacer having a mercapto group is introduced into the carboxy group of the hyaluronic acid and preparing a steryl group in which a spacer having a mercapto group is introduced at the terminal, followed by reacting them oxidatively to form a disulfide bond. At this time, one mercapto group may be reacted with 2-mercaptopyridine to form a disulfide, and then the other one mercapto group may be substituted.

Further, after preparing the hyaluronic acid derivative of the present invention, other substituents may be introduced. For example, 0.1% or more and 99.5% or less, preferably 10% or more and 40% or less of the carboxyl group in the hyaluronic acid derivative substantially composed of the repeating unit (1) and the repeating unit (11) may be converted to —CO—X$^z$ and cross-linked within the molecule or between the molecules including other molecules to gel [wherein, X$^z$is selected from the following groups:

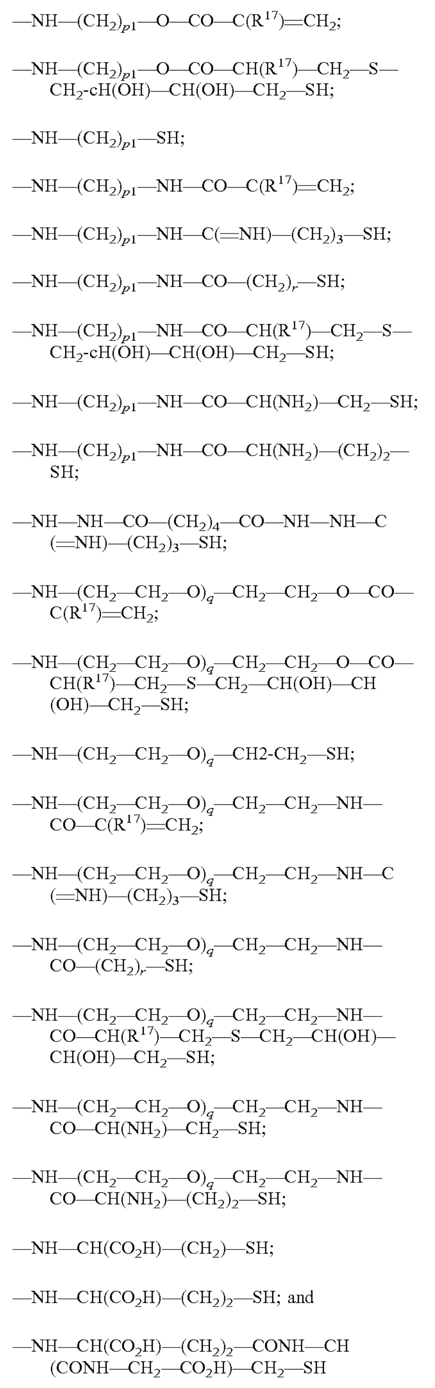

—NH—(CH$_2$)$_{p1}$—O—CO—C(R$^{17}$)═CH$_2$;

—NH—(CH$_2$)$_{p1}$—O—CO—CH(R$^{17}$)—CH$_2$—S—CH$_2$-cH(OH)—CH(OH)—CH$_2$—SH;

—NH—(CH$_2$)$_{p1}$—SH;

—NH—(CH$_2$)$_{p1}$—NH—CO—C(R$^{17}$)═CH$_2$;

—NH—(CH$_2$)$_{p1}$—NH—C(═NH)—(CH$_2$)$_3$—SH;

—NH—(CH$_2$)$_{p1}$—NH—CO—(CH$_2$)$_r$—SH;

—NH—(CH$_2$)$_{p1}$—NH—CO—CH(R$^{17}$)—CH$_2$—S—CH$_2$-cH(OH)—CH(OH)—CH$_2$—SH;

—NH—(CH$_2$)$_{p1}$—NH—CO—CH(NH$_2$)—CH$_2$—SH;

—NH—(CH$_2$)$_{p1}$—NH—CO—CH(NH$_2$)—(CH$_2$)$_2$—SH;

—NH—NH—CO—(CH$_2$)$_4$—CO—NH—NH—C(═NH)—(CH$_2$)$_3$—SH;

—NH—(CH$_2$—CH$_2$—O)$_q$—CH$_2$—CH$_2$—O—CO—C(R$^{17}$)═CH$_2$;

—NH—(CH$_2$—CH$_2$—O)$_q$—CH$_2$—CH$_2$—O—CO—CH(R$^{17}$)—CH$_2$—S—CH$_2$—CH(OH)—CH(OH)—CH$_2$—SH;

—NH—(CH$_2$—CH$_2$—O)$_q$—CH2-CH$_2$—SH;

—NH—(CH$_2$—CH$_2$—O)$_q$—CH$_2$—CH$_2$—NH—CO—C(R$^{17}$)═CH$_2$;

—NH—(CH$_2$—CH$_2$—O)$_q$—CH$_2$—CH$_2$—NH—C(═NH)—(CH$_2$)$_3$—SH;

—NH—(CH$_2$—CH$_2$—O)$_q$—CH$_2$—CH$_2$—NH—CO—(CH$_2$)$_r$—SH;

—NH—(CH$_2$—CH$_2$—O)$_q$—CH$_2$—CH$_2$—NH—CO—CH(R$^{17}$)—CH$_2$—S—CH$_2$—CH(OH)—CH(OH)—CH$_2$—SH;

—NH—(CH$_2$—CH$_2$—O)$_q$—CH$_2$—CH$_2$—NH—CO—CH(NH$_2$)—CH$_2$—SH;

—NH—(CH$_2$—CH$_2$—O)$_q$—CH$_2$—CH$_2$—NH—CO—CH(NH$_2$)—(CH$_2$)$_2$—SH;

—NH—CH(CO$_2$H)—(CH$_2$)—SH;

—NH—CH(CO$_2$H)—(CH$_2$)$_2$—SH; and

—NH—CH(CO$_2$H)—(CH$_2$)$_2$—CONH—CH(CONH—CH$_2$—CO$_2$H)—CH$_2$—SH (wherein, $R^{17}$ is a hydrogen atom or a $C_{1-6}$ alkyl group, p1 is an integer of 2 or more and 10 or less, q is an integer of 1 or more and 200 or less, and r is an integer of 1 or more and 3 or less.)]

The conditions for gelling the hyaluronic acid derivative by chemical cross-linking may be appropriately selected. The cross-linking conditions include a cross-linking method, polymer concentration, cross-linking agent concentration, solvent, solvent pH, salt concentration, temperature, time and the like.

In the step of gelling the hyaluronic acid derivative, by adjusting the reaction conditions for cross-linking, for example, by increasing the polymer concentration during the chemical cross-linking and the introduction rate of the groups capable of cross-linking, it is possible to increase the cross-linking density of the gel to be produced.

When using a cross-linking agent having a group capable of forming a cross-linking at both terminals, the concentration of the cross-linking agent in the step of gelling the hyaluronic acid derivative is preferably such that the group can quickly participate in the cross-linking reaction without excess or deficiency. For example, when a polymer having a methacryloyl group (MA group) introduced is cross-linked by a Michael addition reaction using DTT, MA group: SH group=3:1 to 1:3 is preferable, and 2:1 to 1:2 is particularly preferable.

The solvent in the step of gelling the hyaluronic acid derivative is preferably one capable of sufficiently dissolving the polymer and the cross-linking agent, and although it is not particularly limited, it is preferable to use water, dimethyl sulfoxide (DMSO), dimethylacetamide (DMAc), dimethylformamide (DMF), N-methylpyrrolidone (NMP) and a mixed solvent thereof. It is also possible to mix an organic solvent miscible with these solvents to use. The miscible organic solvent is not limited, and examples thereof include, a methanol, ethanol, propanol, isopropanol, butanol, polyhydric alcohol, acetone, acetonitrile and the like. Examples of the polyhydric alcohol include those similar to those exemplified in the above-mentioned "(B) alcohol", and among them, an ethylene glycol is preferable.

Since the hyaluronic acid derivative forms nanoparticles in an aqueous solution, it is possible to form a nano-sized fine particle gel by cross-linking under a dilute concentration condition, and it can be used as a blood sustained-release carrier or a targeting carrier. The dilute concentration condition refers to 10 mg/mL or less, preferably 5 mg/mL or less, and more preferably 1 mg/mL or less. On the other hand, by cross-linking under a high concentration condition, it is possible to form a bulk gel in which fine particles are cross-linked. This is useful as a subcutaneous sustained release carrier. The high concentration condition is 5 mg/mL or more, preferably 20 mg/mL or more, and more preferably 40 mg/mL.

The step of gelling the hyaluronic acid derivative may be carried out in bulk or in a discontinuous phase such as in an emulsion or a spray droplet. For example, when it is carried out in a W/O emulsion, an aqueous phase in which a polymer, a cross-linking agent or the like is dissolved may be emulsified in a solvent immiscible with water to carry out a gelation reaction. The solvent immiscible with water is not particularly limited, and examples thereof include a hexane, chloroform, dichloromethane, ethyl acetate, medium chain fatty acid triglyceride (MCT), liquid paraffin, soybean oil and the like. A surfactant may be added to stabilize the emulsification. Further, for example, it may be carried out in a solvent capable of being removed such as in supercritical carbon dioxide or PEG. In this case, once an aqueous or organic phase in which polymers and a cross-linking agent are dissolved is emulsified and dispersed in the above solvent, the polymers can be concentrated as a result of desolvation (solvent diffusion) to thereby obtain a gel with a higher cross-linking density.

During or after the step of gelling the hyaluronic acid derivative, additional operations may be performed to stop the cross-linking reaction and to inactivate or wash off residual cross-linking functional groups. Cross-linking functional groups which are not used for the reaction, groups which are attached to only one terminal of cross-linking agent molecules, residual cross-linking agent molecules and so on are preferably removed in terms of safety, storage stability, side reactions with a drug to be encapsulated, etc. Without being limited thereto, for example, when there remain unreacted cross-linking agent molecules, they may be removed by washing with an excessive amount of water. Likewise, for example, when there remain methacryloyl groups substituted onto polymers, an excessive amount of mercaptoethanol or the like may be added to inactivate the methacryloyl groups, followed by washing with an excessive amount of water to remove the excess of mercaptoethanol. Moreover, for example, when there remain mercapto groups, an excessive amount of 3-maleimidopropionic acid, iodoacetic acid or the like may be added to inactivate the mercapto groups, followed by washing with an excessive amount of water to remove the excess of 3-maleimidopropionic acid or iodoacetic acid.

The step of gelling the hyaluronic acid derivative may be followed by a grinding step. Examples of the grinding techniques include grinding with a pestle and mortar, grinding in a mill, and so on. Preferred is grinding in a mill Examples of a mill grinder include rotating disk grinders such as a centrifugal mill (Nihonseiki Kaisha Ltd., Japan) and an impact mill (Dalton Co., Ltd., Japan), Screen mill grinders such as an atomizer (Tokyo Atomizer Mfg. Co., Ltd., Japan), a sample mill (Tokyo Atomizer Mfg. Co., Ltd., Japan), a bantam mill (Tokyo Atomizer Mfg. Co., Ltd., Japan) and an SK mill (Tokken Inc., Japan), jet mills such as an ultra-micro labo jet mill (A-O jet mill, Seishin Enterprise Co., Ltd., Japan), as well as a Linrex mill (Liquid Gas Co., Ltd., Japan) which allows grinding at ultra-low temperatures, with a SK mill and a Linrex mill being preferred.

A drying step may be performed after the step of gelling the hyaluronic acid derivative. Examples of the drying method include ventilation drying, drying in a constant temperature bath, vacuum drying, hot air circulation type drying and the like. The wind speed, drying time, temperature, pressure and the like are appropriately selected as long as the gel of the hyaluronic acid derivative does not decompose or deteriorate.

<<Pharmaceutical Composition>>

The pharmaceutical composition of the present embodiment contains the above hyaluronic acid derivative as a carrier. In the pharmaceutical composition of the present embodiment, it is desirable that the carrier and the drug be directly or indirectly bonded to form a complex and not be free from each other. When the pharmaceutical composition is administered in vivo, the drug is gradually released from the carrier, and good sustained release can be expected. The bond between the carrier and the drug may be covalent or non-covalent, but non-covalent is preferable from the viewpoint of maintaining the activity of the drug.

In the pharmaceutical composition of the present embodiment, the drug preferably forms a complex with a hyaluronic acid derivative as a carrier. It is considered that a complex between the drug and the hyaluronic acid derivative is formed by spontaneous association of the steryl group of the hyaluronic acid derivative in the solvent due to the hydrophobic interaction between the steryl group of the hyaluronic acid derivative and the drug present in the system . . . By forming the complex, the storage stability of the drug is improved, the biological activity is maintained, the sustained release property is improved, the solubility in water is improved, the resistance to stimuli such as heat and light is improved, and aggregation and precipitation are performed. Suppression is expected.

<Drug>

The drug contained in the pharmaceutical composition of the present embodiment is not particularly limited as long as it is a drug that can be used as a drug for humans and animals. For example, proteins, peptides, polysaccharides, nucleic acids, low-molecular-weight compounds and the like can be mentioned. The pharmaceutical composition of the present embodiment preferably contains a biopharmaceutical such as a protein, peptide, nucleic acid or the like having pharmacological activity, or a low-molecular-weight compound in a complex with a hyaluronic acid derivative. By forming a complex, it is expected to improve the chemical stability of the drug, suppress aggregation, suppress decomposition by enzymes, and the like.

[Low-Molecular-Weight Compound]

Examples of the low-molecular-weight compound include anticancer agents (for example, alkylating agents, antimetabolites, alkaloids, etc.), immunosuppressants, anti-inflammatory agents (steroids, non-steroidal anti-inflammatory agents, etc.), anti-rheumatic agents, antibacterial agents (β-lactam antibiotics, aminoglycoside antibiotics, macrolide antibiotics, tetracycline antibiotics, new quinolone antibiotics, sulfa drugs, etc.) and the like.

[Protein and Peptide]

Examples of the protein and peptide include erythropoetin (EPO), granulocyte colony-stimulating factor (G-CSF), interferon-α, β, γ, (INF-α, β, γ), thrombopoetin (TPO), ciliary neurotrophic factor (CNTF), tumor necrosis factor (TNF), tumor necrosis factor binding protein (TNFbp), interleukin-10 (IL-10), FMS-like tyrosine kinase (Flt-3), growth hormone (GH)), insulin, insulin-like growth factor-1 (IGF-1), platelet-derived growth factor (PDGF), interleukin-1 receptor antagonist (IL-1ra), brain-derived neurotrophic factor (BDNF), keratinocyte growth factor (KGF), stem cell factor (SCF), megakaryocyte growth and development factor (MGDF), osteoprotegerin (OPG), leptin, parathyroid hormone (PTH), basic fibroblast growth factor (b-FGF), bone morphogenetic protein (BMP), atrial natriuretic peptide (ANP), brain natriuretic peptide (BNP), C-type natriuretic peptide (CNP), glucagon-like peptide-1 (GLP-1), antigen for vaccine, antibody, diabody, minibody, fragmented antibody, PEGylated protein (eg, PEGylated interferon-α-2a, PEGylated interferon-α-2b, PEGylated GCSF, PEGylated hG11 antagonist B2036, etc.) and the like.

[Nucleic Acid]

Examples of the nucleic acid include DNA, RNA, antisense nucleic acid, decoy nucleic acid, ribozyme, small interfering RNA, nucleic acid aptamer and the like.

<Form>

The pharmaceutical composition of the present embodiment may be a dispersible fine particle solution, a precipitating suspension, or a freeze-dried product. Further, in the case of the freeze-dried product, it may be a precipitation-type sustained-release preparation of a type in which a doctor adds an isotonic solution such as physiological saline to prepare the administration solution at the time of use. In this case, it is considered suitable for a pharmaceutical composition containing an active ingredient that is unstable in a solution state.

When the pharmaceutical composition of the present embodiment is a dispersible fine particle solution or a precipitation suspension, the concentration of the hyaluronic acid derivative in the pharmaceutical composition is preferably 1 mg/mL or more and 200 mg/mL or less, more preferably 4 mg/mL or more and 100 mg or less, even more preferably 4 mg/mL or more and 50 mg/mL or less, and particularly preferably 4 mg/mL or more and 12 mg/mL or less. When the concentration of the hyaluronic acid derivative in the pharmaceutical composition is within the above range, it is possible to achieve improved viscosity when it is used as an injection. In addition, the syringeability of the injection using the hyaluronic acid derivative of the present embodiment can be further improved.

<<Hyaluronic Acid Derivative-Drug Complex>>

In the hyaluronic acid derivative-drug complex of the present embodiment, one or more drugs are bonded to the above hyaluronic acid derivative.

Examples of suitable drugs for forming the hyaluronic acid derivative-drug complex composition of the present embodiment include biopharmaceuticals such as proteins, peptides, nucleic acids or the like, low-molecular-weight compounds, and the like.

The pharmaceutical composition and the hyaluronic acid derivative-drug complex composition of the present embodiment are not limited to the forms already described, and may be in the form of nanoparticles, microparticles, solutions, emulsions, suspensions, gels, micelles, implants, powders, or films. The powder may be produced by pulverizing a solid obtained by freeze-drying or spray-drying, or may be produced from a dried precipitate.

The pharmaceutical composition and the hyaluronic acid derivative-drug complex composition of the present embodiment may be administered via a route such as oral, parenteral, intranasal, intravaginal, intraocular, subcutaneous, intravenous, intramuscular, intracutaneous, intraperitoneal, intracerebral, or intraoral. Further, the pharmaceutical composition and the hyaluronic acid derivative-drug complex composition of the present embodiment are not limited to injections, and may be patch preparations, microneedle preparations, ointments, eye drops, sprays, inhalations, dermal fillers or the like.

Further, the hyaluronic acid derivative of the present embodiment can be used not only as a pharmaceutical composition but also as a cosmetic composition, a test drug composition, a preservative for a medical device, and a surface coating agent.

The cosmetic composition may contain a physiologically active ingredient. The type of physiologically active ingredient is not particularly limited, and examples thereof include an anti-aging agent, a tightening agent, an anti-inflammatory agent, a whitening agent, a moisturizing agent, a blood circulation promoter, vitamins, amino acids, peptides, ceramides, a wound healing promoter, UV protection agent, stimulant relieving agent, cell activator, enzyme ingredient and the like.

The test agent composition may contain a component for testing and other components. As the component for testing, polymer particles, inorganic particles or flat membranes carrying an antibody, or the like may be used. As said other component, carriers, physiological saline, preservatives (sodium azide, benzalkonium chloride, chlorobutanol, etc.), stabilizers (propylene glycol, ascorbic acid, etc.), excipients (lactose, starch, sorbitol, sorbitol, D-mannitol, etc.), buffers (sodium lauryl sulfate, methyl cellulose, carboxymethyl cellulose, hydroxymethyl cellulose, glycerin monostearate, aluminum monostearate, etc.), preservatives (benzalkonium chloride, benzyl alcohol, methylparaben, etc.) or the like may be contained.

Examples of the preservative and surface coating agent for a medical device include thickeners, vitamins, amino acids, peptides, stabilizers, bactericides and the like. Examples of the medical devices include endoscopes, artificial joints, dentitions, stents, contact lenses, catheters, guide wires, finger structures, artificial hearts, artificial muscle fibers and the like.

EXAMPLES

Hereinafter, the present invention will be described in detail with reference to Examples, but these are not intended to limit the scope of the present invention to the Examples.

The methods for measuring and evaluating the physical properties of the hyaluronic acid derivatives produced in the Examples and the Comparative Examples are as follows.

[Physical Property 1]

(Weight-average molecular weight Mw of hyaluronic acid derivative and ratio Mw/Mn of weight-average molecular weight to number-average molecular weight)

The weight-average molecular weight Mw and the number-average molecular weight Mn of the hyaluronic acid derivative were measured using a size exclusion chromatography multi-angle light scattering detector (SEC-MALS). The hyaluronic acid derivative (20 mg) was dissolved in ultrapure water (10 mL) and stirred at room temperature for 12 hours or more to obtain an aqueous hyaluronic acid derivative solution (2 mg/mL). A 300 mM hydroxypropyl-β-cyclodextrin (HP-β-CD) aqueous solution (750 μL) was added to this hyaluronic acid derivative aqueous solution (750 μL), mixed for 10 seconds using a shaker, and incubated at 37° C. for 1 hour. Then, the obtained sample was subjected to SEC-MALS measurement to determine the weight-average molecular weight Mw and the number-average molecular weight Mn. The conditions for SEC-MALS measurement are shown below. Further, the ratio Mw/Mn of the weight-average molecular weight to the number-average molecular weight was calculated by dividing the weight-average molecular weight Mw by the number-average molecular weight Mn obtained from the measurement results of SEC-MALS.

(Measurement Condition)

Column: TSKgel GMPWXL (manufactured by Tosoh Corporation), two

Column temperature: 30° C.

Fluent: 10 mM HP-f-CD-containing phosphate buffered saline (pH7.4)

Flow rate: 1 mL/min

Injection volume: 200 μL

[Physical Property 2]

(Steryl Group Introduction Rate)

The steryl group introduction rate of the hyaluronic acid derivative was determined by $^1$H-NMR measurement. First, dimethyl sulfoxide-$d_6$ (99.9 v/v %, containing 0.05 v/v % trimethylsilyl (TMS), manufactured by FUJIFILM Wako Pure Chemical Corporation) and 20% heavy hydrochloric acid (99.5 v/v %, manufactured by FUJIFILM Wako Pure Chemical Corporation) were mixed at a mass ratio of 99:1 to prepare a measurement solvent. Subsequently, the hyaluronic acid derivative (2 mg) was added to this measurement solvent (0.6 mL), treated with an ultrasonic bath for 30 minutes, completely dissolved, and subjected to $^1$H-NMR measurement. $^1$H-NMR measurement was carried out at a sample temperature of 85° C. using a Fourier transform nuclear magnetic resonance apparatus (FT-NMR apparatus) (ECS400, manufactured by JEOL Ltd.). The steryl group introduction rate is the introduction rate of the cholesteryl group to the hyaluronic acid unit, and was calculated by the following formula using the integrated value of the peak derived from the acetyl group of N-acetyl-D-glucosamine ($COCH_3$, 1.6 ppm or more and 2.0 ppm or less, 3H) and the integrated value of the peak derived from the methyl group in the cholesteryl group ($CH_3$, 0.7 ppm, 3H). Since the peak derived from the cholesteryl group (5H) overlaps with the peak around 1.6 ppm or more and 2.0 ppm or less including the peak derived from the acetyl group of N-acetyl-D-glucosamine, the value calculated by subtracting 5/3 of the integral value of the peak derived from the methyl in the cholesteryl group (0.7 ppm) from the integral value of the peak around 1.6 ppm or more and 2.0 ppm (i.e. integrated value (1.6 ppm or more and 2.0 ppm or less)−integrated value (0.7 ppm)×5/3) was used as the integral value of the peak derived from the acetyl group in N-acetyl-D-glucosamine in the calculation of the steryl group introduction rate.

[Steryl group introduction rate (%)]=[(Integrated value of peak derived from methyl group in cholesteryl group)/(Integrated value of peak derived from acetyl group in N-acetyl-D-glucosamine)]×100=[Integrated value(0.7 ppm)/{Integrated value(1.6 ppm or more and 2.0 ppm or less)−Integrated value(0.7 ppm)×5/3}]×100

[Evaluation 1]

<Strain Rate Dependence Test>

The ability to reduce the viscosity in response to the shear of the hyaluronic acid derivative, that is, the shear-thinning property, was determined by the procedure shown below.

First, ultrapure water was added to the hyaluronic acid derivative, and the mixture was stirred and dissolved for 12 hours or more to obtain an aqueous hyaluronic acid derivative solution at a concentration of 4 mg/mL. This aqueous solution was subjected to a strain rate dependence test. The conditions of the strain rate dependence test are shown below.

(Measurement Condition)

Measuring device: ARES manufactured by TA Instruments

Measurement temperature: 25° C.

Geometry: 50 mmφ cone & plate

Shear rate: 0.25 $s^{-1}$ or more and 1,000 $s^{-1}$ or less

Measuring time: 60 s per point

The shear-thinning property of the hyaluronic acid derivative was calculated by the formula shown below.

[Shear-thinning property]=(Viscosity at shear rate of 1 $s^{-1}$ [mPa·s])/(Viscosity at shear rate of 1,000 $s^{-1}$ [mPa·s])

Preparation of Hyaluronic Acid Derivative

Example 1

(Preparation of hyaluronic acid derivative HA-a1) The hyaluronic acid derivative was prepared according to the following steps 1 to 3.

1. Step 1

(Synthesis of Cholesteryl 6-Aminohexyl Carbamate Hydrochloride)

Cholesteryl 6-aminohexyl carbamate hydrochloride (Chol hydrochloride) was synthesized according to Step 1-1, followed by Step 1-2 shown below.

(Step 1-1)

Triethylamine (TEA, 1.05 mL) was added to a solution of cholesteryl chloroformate (3.37 g, 7.5 mmol) in anhydrous dichloromethane (20 mL) under an argon atmosphere, and the mixture was stirred. Under ice-cooling, 6-(t-butoxycarbonyl)amino-1-aminohexane (1.12 mL, 5 mmol) was added dropwise, and the mixture was stirred as it was under ice-cooling for 30 minutes and then heated to room temperature, followed by stirring overnight. The reaction mixture was washed with ultrapure water and saturated brine, dried over anhydrous magnesium sulfate, and the solvent was distilled off under reduced pressure. The obtained residue was purified by silica gel column chromatography (eluent: ethyl acetate: n-hexane=1:4), the fractions containing the desired product were combined, and the solvent was distilled off under reduced pressure.

(Step 1-2)

The obtained residue was dissolved in ethyl acetate (40 mL), and then 4N hydrochloric acid/ethyl acetate solution (40 mL) was added, followed by stirring overnight at room temperature. The resulting precipitate was recovered by centrifugation. The obtained solid was washed with ethyl acetate 4 times, and then dried under reduced pressure to obtain 1.2 g of cholesteryl 6-aminohexyl carbide hydrochloride (Chol hydrochloride). The $^1$H-NMR spectrum of the product (ECS400, manufactured by JEOL Ltd., EtOH-d6) is shown in FIG. 1.

2. Step 2

(Preparation of Tetrabutylammonium (TBA) Salt of Hyaluronic Acid)

The TBA salt of hyaluronic acid (HA-TBA) was prepared according to Step 2-1, followed by Step 2-2 shown below.

(1) Step 2-1

DOWNEX (registered trademark) 50WX-8-400 (manufactured by Aldrich company) was suspended in ultrapure water, and the resin was washed with ultrapure water about 3 times by decantation. A 40 wt % tetrabutylammonium hydroxide aqueous solution (TBA-OH) (manufactured by Aldrich company) was added in an amount of about 1.5-fold molar equivalents relative to the cation-exchange capacity of the resin, followed by stirring for 30 minutes. The excess TBA-OH solution was removed by decantation, and then the resin was washed with an excess amount of ultrapure water to obtain a TBA salt of the cation exchange resin.

(2) Step 2-2

Figure 2:
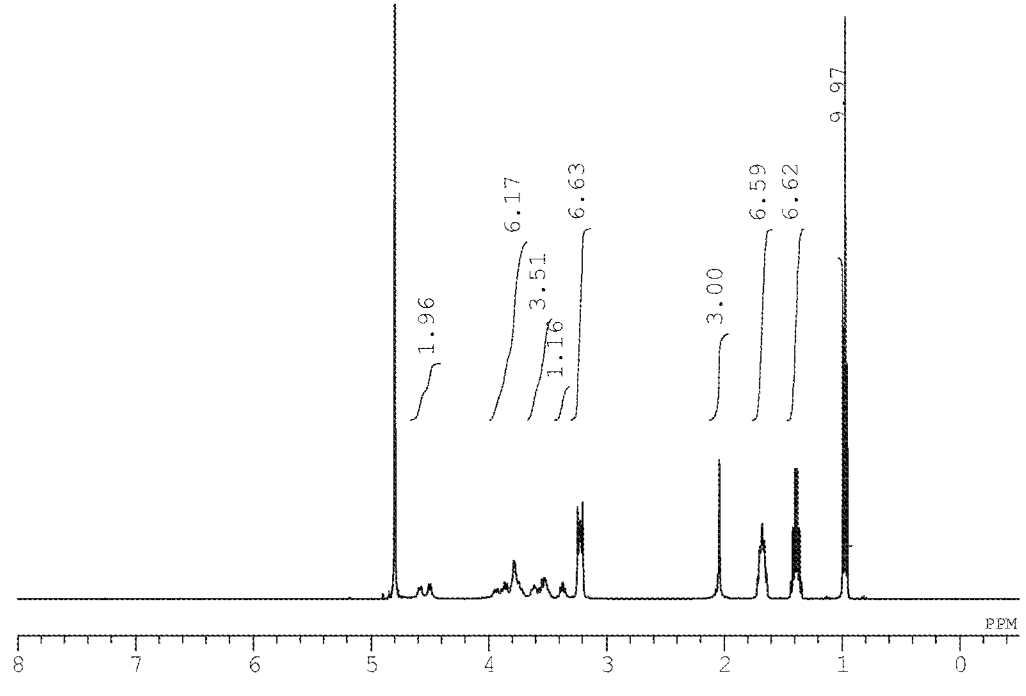
FIG. 2 is a $^1$H-NMRspectrum of tetrabutylammonium (TBA) salt of hyaluronic acid (HA) in Example 1.

A raw material hyaluronic acid sodium salt (HA-Na) having a weight-average molecular weight of 50,000 (50 kDa) was dissolved in ultrapure water at a concentration of 15 mg/mL. The suspension of the TBA salt of the cation exchange resin in "(1) Step 2-1" was added in an amount of 5-fold molar equivalents relative to HA units (unit molecular weight: 401.3) in terms of the ion exchange capacity of the resin. After stirring for 15 minutes, filtration was performed using a 0.45 μm filter, and the filtrate was freeze-dried to obtain a TBA salt of hyaluronic acid (HA-TBA) as a white solid. The $^1$H-NMR spectrum of the product (ECS400, manufactured by JEOL Ltd., EtOH-$d_6$) is shown in FIG. 2.

3. Step 3

Figure 3:
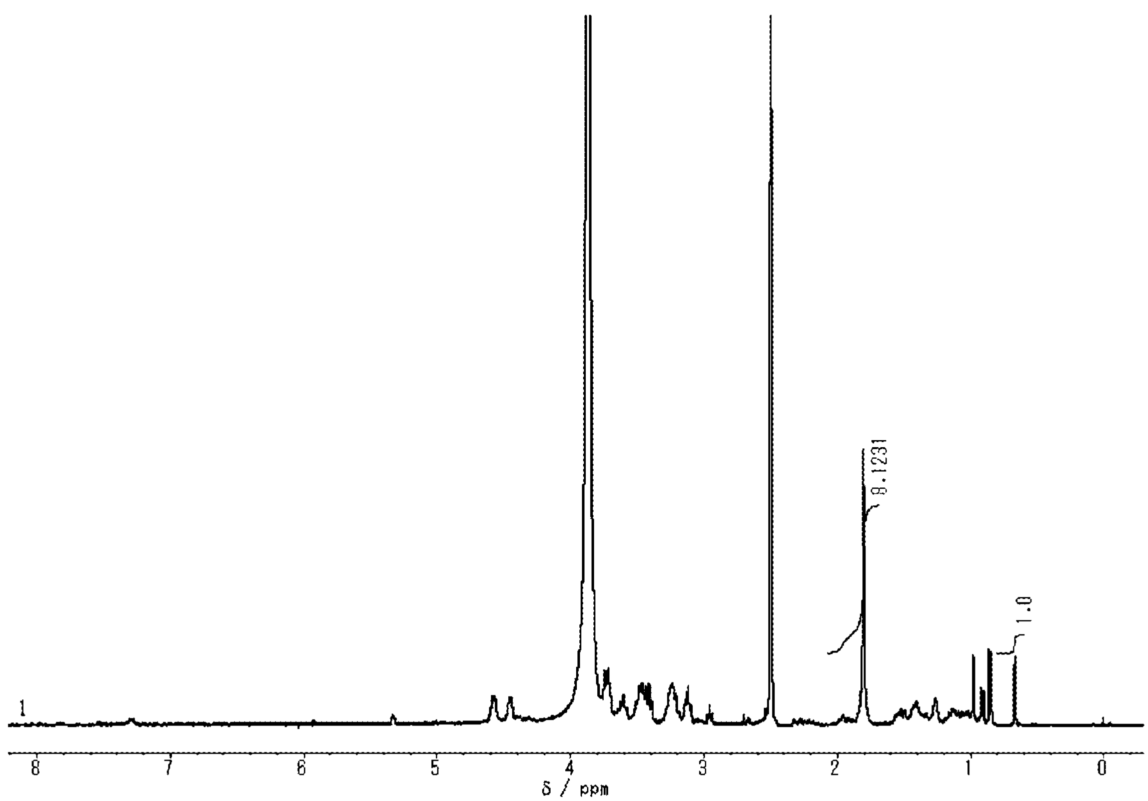
FIG. 3 is a $^1$H-NMRspectrum of HA derivative (HA-$C_6$-Chol) introduced with 6-aminohexyl carbamate in Example 1.

An anhydrous DMSO solution (10 mg/mL) of HA-TBA prepared in "2. (2) Step 2-2" was prepared. Then, the Chol hydrochloride synthesized in "1. Step 1" was added so that the amount of Chol hydrochloride relative to the disaccharide repeating unit (HA unit) present in the HA-TBA was 15/100 in molar ratio. Next, 4-(4,6-dimethoxy-1,3,5-triazine-2-yl)-4-methylmorpholinium chloride (DMT-MM) was added so that the amount of DMT-MM relative to HA unit was 21.6/100 in molar ratio, followed by stirring overnight at room temperature. The reaction solution was dialyzed against 0.3 M ammonia acetate/DMSO solution, 0.15 M NaCl aqueous solution in this order, and ultrapure water (Spectra/Por 4, molecular weight cut-off (MWCO): 12,000 or more and 14,000 or less). The obtained dialysate was freeze-dried to obtain the desired product (HA-$C_6$-Chol) as a white solid. The $^1$H-NMR spectrum of the product is shown in FIG. 3. A peak derived from the acetyl group of N-acetyl-D-glucosamine ($COCH_3$, 1.6 ppm or more and 2.0 ppm or less, 3H) and a peak derived from the methyl group in the cholesteryl group ($CH_3$, 0.7 ppm, 3H) were confirmed.

Examples 2 to 31

(Preparation of Hyaluronic Acid Derivatives HA-a2 to HA-a31)

Each hyaluronic acid derivative was obtained in the same manner as in Example 1 except that in "2. (2) Step 2-2", raw material hyaluronic acid sodium salts (HA-Na) having molecular weights shown in Tables 1 to 7 were used, and in "3. Step 3", the amount of Chol hydrochloride relative to HA unit, and the amount of DMT-MM relative to HA unit were the ratios shown in Tables 1 and 2. $^1$H-NMR measurement was carried out on the obtained hyaluronic acid derivatives, and in each hyaluronic acid derivative, the peak derived from the acetyl group of N-acetyl-D-glucosamine ($COCH_3$, 1.6 ppm or more and 2.0 ppm or less, 3H).), and the peak derived from the methyl group in cholesteryl group ($CH_3$, 0.7 ppm, 3H) were confirmed.

Example 32

(Hyaluronic Acid Derivative HA-a32)

Each hyaluronic acid derivative was obtained in the same manner as in Example 1 except that in "2. (2) Step 2-2", raw material hyaluronic acid sodium salts (HA-Na) having molecular weights shown in Table 8 were used, in "3. Step 3", the amount of Chol hydrochloride relative to HA unit, and the amount of DMT-MM relative to HA unit were the molar ratios shown in Tables 1 and 2, and 1,6-diaminohexane was further added. $^1$H-NMR measurement was carried out on the obtained hyaluronic acid derivatives, and in each hyaluronic acid derivative, the peak derived from the acetyl group of N-acetyl-D-glucosamine ($COCH_3$, 1.6 ppm or more and 2.0 ppm or less, 3H).), and the peak derived from the methyl group in cholesteryl group ($CH_3$, 0.7 ppm, 3H) were confirmed.

Comparative Example 1

(Preparation of Hyaluronic Acid Derivative HA-b1)

The hyaluronic acid derivative was prepared according to the following steps 1 to 3.

1. Step 1

(Synthesis of Cholesteryl 6-Aminohexyl Carbamate Hydrochloride)

Chol hydrochloride was synthesized using the same method as in Example 1.

2. Step 2

(Preparation of Tetrabutylammonium (TBA) Salt of Hyaluronic Acid)

The TBA salt of hyaluronic acid (HA-TBA) was prepared according to Step 2-1 and Step 2-2, followed by Step 2-3 shown below.

(1) Step 2-1

Hyaluronic acid sodium salt (HA-Na, 50 kDa, Mw/Mn: 1.2) was dissolved to a concentration of 10 mg/mL in ultrapure water. This solution was dialyzed against ultrapure water (Spectra/Por 6, molecular weight cut-off (MWCO): 50,000). The obtained dialysate was freeze-dried to obtain the desired product (HA-Na) as a white solid.

The weight-average molecular weight and the number-average molecular weight of the product were measured using a size exclusion chromatography multi-angle light scattering detector (SEC-MALS), and it was confirmed that the weight-average molecular weight Mw was 50,000 and Mw/Mn (polydispersity) was 1.1.

(2) Step 2-2

The TBA salt of the cation exchange resin was prepared using the same method as in "2. (1) Step 2-1" of Example 1.

(3) Step 2-3

A TBA salt of hyaluronic acid (HA-TBA) as a white solid was obtained in the same manner as in "2. (2) Step 2-2" of Example 1, except that a hyaluronic acid sodium salt (HA-Na) having a weight-average molecular weight Mw of 50,000 (50 k) obtained in the above "(1) Step 2-1" was used.

3. Step 3

A desired product (HA-$C_6$-Chol) as a white solid was obtained in the same manner as in "3. Step 3" of Example 1, except that the HA-TBA obtained in "2. (3) Step 2-3" above was used. $^1$H-NMR measurement was carried out on the obtained HA-$C_6$-Chol, and the peak derived from the acetyl group in N-acetyl-D-glucosamine ($COCH_3$, 1.6 ppm or more and 2.0 ppm or less, 3H) and a peak derived from the methyl group in cholesteryl group ($CH_3$, 0.7 ppm, 3H) were confirmed.

Comparative Examples 2 to 7

(Hyaluronic Acid Derivatives HA-b2 to HA-b7)

Each hyaluronic acid derivative was obtained in the same manner as in Comparative Example 1 except that in "2. (1) Step 2-1" of Comparative Example 1, hyaluronic acid sodium salts having molecular weights and Mw/Mn (polydispersity) shown in Table 2 were used, and in "3. Step 3" of Comparative Example 1, the amount of Chol hydrochloride relative to HA unit, and the amount of DMT-MM relative to HA unit were the molar ratios shown in Tables 2 to 7. $^1$H-NMR measurement was carried out on the obtained hyaluronic acid derivatives, and in each hyaluronic acid derivative, the peak derived from the acetyl group of N-acetyl-D-glucosamine ($COCH_3$, 1.6 ppm or more and 2.0 ppm or less, 3H).), and the peak derived from the methyl group in the cholesteryl group ($CH_3$, 0.7 ppm, 3H) were confirmed.

With respect to the hyaluronic acid derivatives obtained in the Examples and the Comparative Examples, each physical property was measured by the above-mentioned method, and various evaluations were carried out. The results are shown in Tables 1 to 8.

TABLE 1

| Hyaluronic acid derivative | | Ex. 1 HA-a1 | Ex. 2 HA-a2 | Ex. 3 HA-a3 | Ex. 4 HA-a4 | Ex. 5 HA-a5 | Com. Ex. 1 HA-b1 |
|---|---|---|---|---|---|---|---|
| Composition | Molecular weight of HA-Na | 50 kDa | 50 kDa | 50 kDa | 50 kDa | 50 kDa | 50 kDa |
| | Molar ratio of HA nunit/ Chol hydrochloride/ DMT-MM | 100/15/21.6 | 100/15/21.6 | 100/15/21.6 | 100/15/21.6 | 100/15/21.6 | 100/15/21.6 |
| | Steryl group introduction rate (%) | 15 | 15 | 15 | 15 | 15 | 15 |
| | Mw of hyaluronic acid derivative | 53 kDa | 52 kDa | 52 kDa | 51 kDa | 51 kDa | 53 kDa |
| | Mw/Mn | 1.2 | 1.3 | 1.8 | 2.1 | 2.9 | 1.1 |
| Evaluation | Viscosity at shear rate of 1 $s^{-1}$ (mPa · s) | 10.8 | 10.8 | 11 | 18.9 | 5.9 | 11.9 |
| | Viscosity at shear rate of 1,000 $s^{-1}$ (mPa · s) | 6 | 5.2 | 3.1 | 3.2 | 2.9 | 7.9 |
| | Shear-thinning property | 1.8 | 2.1 | 3.5 | 6 | 2 | 1.5 |

TABLE 2

| Hyaluronic acid derivative | | Ex. 6 HA-a6 | Ex. 7 HA-a7 | Ex. 8 HA-a8 | Ex. 9 HA-a9 | Ex. 10 HA-a10 | Com. Ex. 2 HA-b2 |
|---|---|---|---|---|---|---|---|
| Composition | Molecular weight of HA-Na | 120 kDa | 120 kDa | 120 kDa | 120 kDa | 120 kDa | 120 kDa |
| | Molar ratio of HA nunit/ Chol hydrochloride/ DMT-MM | 100/15/21.6 | 100/15/21.6 | 100/15/21.6 | 100/15/21.6 | 100/15/21.6 | 100/15/21.6 |
| | Steryl group introduction rate (%) | 15 | 15 | 15 | 15 | 15 | 15 |

TABLE 2-continued

| Hyaluronic acid derivative | | Ex. 6 HA-a6 | Ex. 7 HA-a7 | Ex. 8 HA-a8 | Ex. 9 HA-a9 | Ex. 10 HA-a10 | Com. Ex. 2 HA-b2 |
|---|---|---|---|---|---|---|---|
| Evaluation | Mw of hyaluronic acid derivative | 132 kDa | 131 kDa | 131 kDa | 130 kDa | 129 kDa | 134 kDa |
| | Mw/Mn | 1.2 | 1.3 | 1.5 | 1.7 | 2.4 | 1.1 |
| | Viscosity at shear rate of 1 $s^{-1}$ (mPa · s) | 872 | 756.3 | 732.1 | 925.5 | 557.4 | 881 |
| | Viscosity at shear rate of 1,000 $s^{-1}$ (mPa · s) | 34.7 | 24.5 | 20.5 | 15.1 | 14.7 | 59 |
| | Shear-thinning property | 25.1 | 30.9 | 35.7 | 61.3 | 37.9 | 14.9 |

TABLE 3

| Hyaluronic acid derivative | | Ex. 11 HA-a11 | Com. Ex. 3 HA-b3 |
|---|---|---|---|
| Composition | Molecular weight of HA-Na | 35 kDa | 35 kDa |
| | Molar ratio of HA nunit/ Chol hydrochloride/ DMT-MM | 100/15/21.6 | 100/15/21.6 |
| | Steryl group introduction rate (%) | 15 | 15 |
| | Mw of hyaluronic acid derivative | 35 kDa | 35 kDa |
| | Mw/Mn | 1.7 | 1.1 |

TABLE 3-continued

| Hyaluronic acid derivative | | Ex. 11 HA-a11 | Com. Ex. 3 HA-b3 |
|---|---|---|---|
| Evaluation | Viscosity at shear rate of 1 $s^{-1}$ (mPa · s) | 5.4 | 6.6 |
| | Viscosity at shear rate of 1,000 $s^{-1}$ (mPa · s) | 2.7 | 5 |
| | Shear-thinning property | 2 | 1.3 |

TABLE 4

| Hyaluronic acid derivative | | Ex. 12 HA-a12 | Ex. 13 HA-a13 | Ex. 14 HA-a14 | Ex. 15 HA-a15 | Ex. 16 HA-a16 | Ex. 17 HA-a17 | Com. Ex. 4 HA-b4 |
|---|---|---|---|---|---|---|---|---|
| Composition | Molecular weight of HA-Na | 35 kDa | 35 kDa | 35 kDa | 35 kDa | 35 kDa | 35 kDa | 35 kDa |
| | Molar ratio of HA nunit/ Chol hydrochloride/ DMT-MM | 100/19/26.6 | 100/19/26.6 | 100/19/26.6 | 100/19/26.6 | 100/19/26.6 | 100/19/26.6 | 100/19/26.6 |
| | Steryl group introduction rate (%) | 19 | 19 | 19 | 19 | 19 | 19 | 19 |
| | Mw of hyaluronic acid derivative | 35 kDa | 35 kDa | 35 kDa | 35 kDa | 35 kDa | 35 kDa | 35 kDa |
| | Mw/Mn | 1.2 | 1.3 | 1.5 | 1.7 | 2.1 | 2.9 | 1.1 |
| Evaluation | Viscosity at shear rate of 1 $s^{-1}$ (mPa · s) | 5.2 | 5.2 | 5.1 | 5 | 6.3 | 4.7 | 6 |
| | Viscosity at shear rate of 1,000 $s^{-1}$ (mPa · s) | 2.8 | 2.6 | 2.4 | 2.3 | 2.3 | 2.2 | 4.5 |
| | Shear-thinning property | 1.9 | 2 | 2.1 | 2.2 | 2.7 | 2.1 | 1.3 |

TABLE 5

| Hyaluronic acid derivative | | Ex. 18 HA-a18 | Ex. 19 HA-a19 | Ex. 20 HA-a20 | Ex. 21 HA-a21 | Ex. 22 HA-a22 | Com. Ex. 5 HA-b5 |
|---|---|---|---|---|---|---|---|
| Composition | Molecular weight of HA-Na | 10 kDa | 10 kDa | 10 kDa | 10 kDa | 10 kDa | 10 kDa |
| | Molar ratio of HA nunit/ Chol hydrochloride/ DMT-MM | 100/44/58 | 100/44/58 | 100/44/58 | 100/44/58 | 100/44/58 | 100/44/58 |

TABLE 5-continued

| Hyaluronic acid derivative | | Ex. 18 HA-a18 | Ex. 19 HA-a19 | Ex. 20 HA-a20 | Ex. 21 HA-a21 | Ex. 22 HA-a22 | Com. Ex. 5 HA-b5 |
|---|---|---|---|---|---|---|---|
| | Steryl group introduction rate (%) | 43 | 43 | 43 | 43 | 43 | 43 |
| | Mw of hyaluronic acid derivative | 10 kDa | 10 kDa | 10 kDa | 10 kDa | 10 kDa | 10 kDa |
| | Mw/Mn | 1.3 | 1.5 | 1.7 | 2.1 | 2.9 | 1.1 |
| Evaluation | Viscosity at shear rate of 1 $s^{-1}$ (mPa · s) | 3 | 3.3 | 1.8 | 1.9 | 1.9 | 1.9 |
| | Viscosity at shear rate of 1,000 $s^{-1}$ (mPa · s) | 1.5 | 1.5 | 1.4 | 1.3 | 1.3 | 1.9 |
| | Shear-thinning property | 2 | 2.1 | 1.3 | 1.5 | 1.5 | 1 |

TABLE 6

| Hyaluronic acid derivative | | Ex. 23 HA-a23 | Ex. 24 HA-a24 | Ex. 25 HA-a25 | Ex. 26 HA-a26 | Ex. 27 HA-a27 | Com. Ex. 6 HA-b6 |
|---|---|---|---|---|---|---|---|
| Composition | Molecular weight of HA-Na | 10 kDa | 10 kDa | 10 kDa | 10 kDa | 10 kDa | 10 kDa |
| | Molar ratio of HA nunit/ Chol hydrochloride/ DMT-MM | 100/34/45 | 100/34/45 | 100/34/45 | 100/34/45 | 100/34/45 | 100/34/45 |
| | Steryl group introduction rate (%) | 33 | 33 | 33 | 33 | 33 | 33 |
| | Mw of hyaluronic acid derivative | 10 kDa | 10 kDa | 10 kDa | 10 kDa | 10 kDa | 10 kDa |
| | Mw/Mn | 1.3 | 1.5 | 1.7 | 2.1 | 2.9 | 1.1 |
| Evaluation | Viscosity at shear rate of 1 $s^{-1}$ (mPa · s) | 3.6 | 3.7 | 4.3 | 4.2 | 3.8 | 2.7 |
| | Viscosity at shear rate of 1,000 $s^{-1}$ (mPa · s) | 2.4 | 2.4 | 2.3 | 2.3 | 2.1 | 2.6 |
| | Shear-thinning property | 1.5 | 1.5 | 1.9 | 1.8 | 1.8 | 1 |

TABLE 7

| Hyaluronic acid derivative | | Ex. 28 HA-a28 | Ex. 29 HA-a29 | Ex. 30 HA-a30 | Ex. 31 HA-a31 | Com. Ex. 7 HA-b7 |
|---|---|---|---|---|---|---|
| Composition | Molecular weight of HA-Na | 10 kDa | 10 kDa | 10 kDa | 10 kDa | 10 kDa |
| | Molar ratio of HA nunit/ Chol hydrochloride/ DMT-MM | 100/8/11.2 | 100/8/11.2 | 100/8/11.2 | 100/8/11.2 | 100/8/11.2 |
| | Steryl group introduction rate (%) | 8 | 8 | 8 | 8 | 8 |
| | Mw of hyaluronic acid derivative | 10 kDa | 10 kDa | 10 kDa | 10 kDa | 10 kDa |
| | Mw/Mn | 1.3 | 1.5 | 2.1 | 2.9 | 1.1 |
| Evaluation | Viscosity at shear rate of 1 $s^{-1}$ (mPa · s) | 3.3 | 3.4 | 3.7 | 3.5 | 2.5 |
| | Viscosity at shear rate of 1,000 $s^{-1}$ (mPa · s) | 2.1 | 2 | 2 | 1.9 | 2.4 |
| | Shear-thinning property | 1.6 | 1.7 | 1.9 | 1.8 | 1 |

TABLE 8

| | Hyaluronic acid derivative | Ex. 32 HA-a32 | Com. Ex. 4 HA-b4 |
|---|---|---|---|
| Composition | Molecular weight of HA-Na | 10 kDa | 35 kDa |
| | Molar ratio of HA nunit/ Chol hydrochloride/ 1,6-diaminohexane/ DMT-MM | 100/19/0.3/26.6 | 100/19/0/26.6 |
| | Steryl group introduction rate (%) | 19 | 19 |
| | Mw of hyaluronic acid derivative | 35 kDa | 35 kDa |
| | Mw/Mn | 2.1 | 1.1 |
| Evaluation | Viscosity at shear rate of 1 $s^{-1}$ (mPa · s) | 5.5 | 6 |
| | Viscosity at shear rate of 1,000 $s^{-1}$ (mPa · s) | 2.6 | 4.5 |
| | Shear-thinning property | 2.1 | 1.3 |

As shown in Table 1, in the hyaluronic acid derivatives HA-a1 to HA-a5 (Examples 1 to 5) having a weight-average molecular weight Mw of 50 kDa and Mw/Mn (polydispersity) of 1.11 or more, the shear-thinning property was as good as 1.8 or more to 6.0 or less. In addition, the viscosity when a large shear was applied (shear rate: 1,000 $s^{-1}$) was as low as 2.9 mPa·s or more and 6.0 mPa·s or less, which contributed to the improvement of syringeability. On the other hand, in the hyaluronic acid derivative HA-b1 (Comparative Example 1) having a weight-average molecular weight Mw of 50 kDa and a polydispersity of 1.1, the shear-thinning property was 1.5, and the viscosity when a large shear was applied (shear rate: 1,000 $s^{-1}$) was 7.9 mPa·s, which was poor. Further, the shear-thinning property was improved when the polydispersity was 1.3 (Example 2) compared with when it was 1.2 (Example 1).

Further, also as shown in Table 2, the hyaluronic acid derivatives HA-a6 to HA-a10 (Examples 5 and 6) having a weight-average molecular weight Mw of 120 kDa and a polydispersity of 1.11 or more showed an improved shear-thinning property compared with Comparative Examples 2 in which the polydispersity was 1.1.

Further, in the hyaluronic acid derivatives HA-a3, HA-a9 and HA-a10 (Examples 3, 9 and 10) the approximately the same polydispersity but different weight-average molecular weights, there was a tendency in which the shear-thinning property was improved as the weight-average molecular weight increased.

As shown in Table 4, in the case where the introduction rate of the steryl group was changed to 19%, the hyaluronic acid derivatives having a polydispersity of larger than 1.11 also showed a lower viscosity at the shear rate of 1,000 $s^{-1}$ and an improved shear-thinning property, compared with Comparative Example 4 in which the polydispersity was 1.1.

As shown in Table 5, in the hyaluronic acid derivatives HA-a19 and HA-a20 (Examples 19 and 20) having a weight-average molecular weight Mw of 10 kDa and a polydispersity of 1.5 or more and 1.7 or less, the shear-thinning property was 1.3 or more and 2.1 or less, and the viscosity when a large shear was applied (1,000 $s^{-1}$) was 1.4 mPa·s or more and 1.5 mPa·s or less, which was good. On the other hand, the hyaluronic acid derivative HA-b5 (Comparative Example 5) having a polydispersity of 1.1 showed a shear-thinning property of 1.0 and a viscosity of 1.9 mPa·s when a large of shear was applied (1,000 $s^{-1}$), which was poor.

Further, as shown in Table 6, in the hyaluronic acid derivative HA-a25 (Example 25) having a weight-average molecular weight Mw of 10 kDa, a steryl group introduction rate of 33%, and a polydispersity of 1.7, the shear-thinning property was 1.9, the viscosity when a large shear was applied (1,000 $s^{-1}$) was 2.3 mPa·s, which was good. On the other hand, the hyaluronic acid derivative HA-b6 (Comparative Example 6) having a polydispersity of 1.1 showed a shear-thinning property of 1.0 and a viscosity of 2.6 mPa·s when a large shear was applied (1,000 $s^{-1}$), which was poor.

Further, as shown in Table 7, in the case where the weight-average molecular weight Mw was 10 kDa and the steryl group introduction rate was 8%, the hyaluronic acid derivatives having a polydispersity of larger than 1.11 also showed an improved shear-thinning property compared with the hyaluronic acid derivative having a polydispersity of 1.1.

Further, in the hyaluronic acid derivatives HA-a20, HA-a25, and HA-a30 (Examples 20, 25, and 30) having the same polydispersity but different steryl group introduction rates, there was a tendency in which the shear-thinning property was improved as the steryl group introduction rate decreased.

As shown in Table 8, in the case where the hyaluronic acid derivative HA-a32 having a weight-average molecular weight of 35 kDa was obtained by cross-linking the raw material HA-Na having a weight-average molecular weight of 10 kDa, the hyaluronic acid derivative showed an improved shear-thinning property compared with the hyaluronic acid derivative HA-b4 (Comparative Example 4) having a low polydispersity of 1.1, when the weight-average molecular weights were the same. From the results, it can be concluded that the final molecular weight and molecular weight distribution are important, not the raw material.

Example 33

(Complexing of Hyaluronic Acid Derivative and Protein)

The hyaluronic acid derivative HA-a25 obtained in Example 25 was dissolved in pure water at a concentration of 45.0 mg/mL, and 1.0 mL of the obtained hyaluronic acid derivative HA-a25 aqueous solution and 0.5 mL of a separately dissolved hGH (human growth hormone) aqueous solution (9 mg/mL) were mixed, followed by incubating at 37° C. for 24 hours to obtain a composite solution of 30 mg/mL hyaluronic acid derivative HA-a25 and 3 mg/mL hGHcan be obtained. Then, 1.5 mL of 2×PBS was added to form a precipitate of a complex of the hyaluronic acid derivative HA-a10 and hGH. Centrifugation was performed for 10 minutes under the conditions equivalent to 9000 G, and gel permeation chromatograph (GPC) measurement was carried on the supernatant (measurement conditions are shown below). As a result, no peak derived from hGH was observed and it was confirmed that the hyaluronic acid derivative HA-a10 and hGH were completely complexed.

(GPC Condition)

Device: HLC8320-GPC (manufactured by Tosoh)
Column: G2000SWXL
Eluent: 10 mM PBS (pH 7.4)
Flow rate: 1 mL/min
Injection volume: 50 µL
Detector: RI or UV280 nm
Temperature: 30° C.

Example 34

(Complexing of Hyaluronic Acid Derivative and PEGylated Protein)

A complex of the hyaluronic acid derivative HA-a25 and the PEGylated G-CSF was obtained in the same manner as in Example 33 except that the PEGylated G-CSF was used instead of hGH. Further, in the GPC measurement under the same conditions as in Example 33, no peak derived from PEGylated 6-CSF was observed in the supernatant, and it was confirmed that the hyaluronic acid derivative HA-a25 and the PEGylated G-CSF were completely complexed.

Example 35

(Complexing of Hyaluronic Acid Derivative and Poorly Soluble Drug)

The hyaluronic acid derivative HA-a25 obtained in Example 25 was dissolved in pure water at a concentration of 31.6 mg/mL, and 0.95 mL of the obtained hyaluronic acid derivative HA-a25 aqueous solution and 0.05 mL of a separately dissolved cyclosporin A methanol solution (30 mg/mL) were mixed, followed by incubating at 4° C. for 16 hours to obtain a composite solution of 30 mg/mL hyaluronic acid derivative HA-a25 and 3 mg/mL cyclosporin A. Then, 1.5 mL of 2×PBS was added to form a precipitate of a complex of the hyaluronic acid derivative HA-a25 and cyclosporin A. Centrifugation was performed for 10 minutes under conditions equivalent to 9000 G, and high-performance liquid chromatograph (HPLC) measurement was carried on the supernatant. As a result, no peak derived from cyclosporin A was observed, and it was confirmed that the hyaluronic acid derivative HA-a25 and cyclosporin A were completely complexed.

(HPLC Conditions)

Device: HPLC system Extrema (manufactured by JASCO Corporation)
Column: Inertsil ODS 5 μm
Mobile phase: 0.1 v/v % TFA: 90 v/v % Acetonitrile: 10 v/v % water
Flow rate: 1 mL/min
Injection volume: 30 μL
Detector: UV (210 nm)
Temperature: 40° C.

INDUSTRIAL APPLICABILITY

According to the hyaluronic acid derivative of the present embodiment, it is possible to provide a hyaluronic acid derivative having excellent syringeability.

The invention claimed is:

1. A hyaluronic acid derivative having a steryl group introduced therein, wherein a ratio Mw/Mn of a weight-average molecular weight Mw to a number-average molecular weight Mn of the hyaluronic acid derivative is 1.2 or more and less than 3.0, wherein the Mw and the Mn are measured by size exclusion chromatography multi-angle light scattering detector, SEC-MALS, by dissolving the hyaluronic acid derivative in ultrapure water, and stirring to obtain an aqueous hyaluronic acid derivative solution of concentration 2 mg/mL; mixing 750 mL of a 300 mM hydroxypropyl-β-cyclodextrin (HP-β-CD) aqueous solution with 750 μL of the hyaluronic acid derivative aqueous solution to obtain a mixture; incubating the mixture at 37° C. for 1 hour; and obtaining a SEC-MALS measurement of the incubated mixture under the following conditions:

column: two TSKgel GMPWXL columns
column temperature: 30° C.
eluent: 10 mM HP-β-CD-containing phosphate buffered saline (pH 7.4)
flow rate: 1 mL/min
injection volume: 200 μL to determine the Mw and the Mn, and wherein the hyaluronic acid derivative has a repeating unit represented by the following general formula (I), (I)

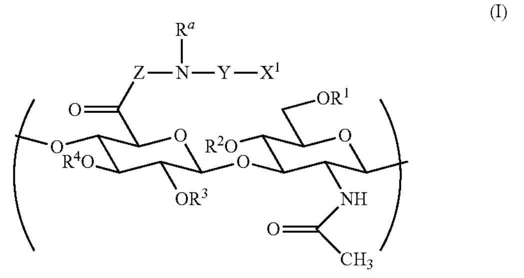

in the formula, $R^1$, $R^2$, $R^3$ and $R^4$ are each independently selected from the group consisting of a hydrogen atom, a $C_{1-6}$ alkyl, a formyl and a $C_{1-6}$ alkyl carbonyl;

Z represents a single bond or a peptide linker having 2 or more and 30 or less amino acid residues;

$X^1$ is a group selected from the group consisting of groups represented by the following formulas:

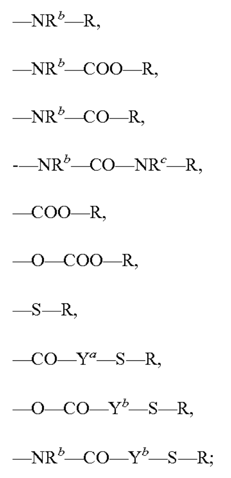

$—NR^b—R$, $—NR^b—COO—R$, $—NR^b—CO—R$, $—NR^b—CO—NR^c—R$, $—COO—R$, $—O—COO—R$, $—S—R$, $—CO—Y^a—S—R$, $—O—CO—Y^b—S—R$, $—NR^b—CO—Y^b—S—R$;

$R^a$, $R^b$ and $R^c$ are each independently selected from the group consisting of a hydrogen atom, a $C_{1-20}$ alkyl, an amino $C_{2-20}$ alkyl and a hydroxy $C_{2-20}$ alkyl, where an alkyl moiety of the groups may be inserted with a group selected from the group consisting of —O— and $—NR^f—$;

$R^f$ is selected from the group consisting of a hydrogen atom, a $C_{1-12}$ alkyl, an amino $C_{2-12}$ alkyl and a hydroxy $C_{2-12}$ alkyl, and an alkyl moiety of the groups may be inserted with a group selected from the group consisting of —O— and —NH—;

R is a steryl group;

Y is a $C_{2-30}$ alkylene or $—(CH_2CH_2O)_m—CH_2CH_2—$, where the alkylene may be inserted with a group selected from the group consisting of —O—, $—NR^g$- and —S—S—;

$R^g$ is selected from the group consisting of a hydrogen atom, a C1-20 alkyl, an amino C2-20 alkyl and a hydroxy C2-20 alkyl, and an alkyl moiety of the groups may be inserted with a group selected from the group consisting of —O— and —NH—;

$Y^a$ is a $C_{1-5}$ alkylene;

$Y^b$ is a $C_{2-8}$ alkylene or a $C_{2-8}$ alkenylene;

m is an integer of 1 or more and 100 or less.

2. The hyaluronic acid derivative according to claim 1, wherein the hyaluronic acid derivative has a weight-average molecular weight of 3,000 or more and 160,000 or less.

3. The hyaluronic acid derivative according to claim 1, wherein an introduction rate of the steryl group to the hyaluronic acid derivative is 6% or more and less than 60%.

4. The hyaluronic acid derivative according to claim 1, wherein R is a cholesteryl group.

5. The hyaluronic acid derivative according to claim 1, wherein the ratio Mw/Mn of the weight-average molecular weight Mw to the number-average molecular weight Mn of the hyaluronic acid derivative is 1.2 or more and 2.9 or less.

6. The hyaluronic acid derivative according to claim 1, wherein the hyaluronic acid derivative has a weight-average molecular weight of 7,000 or more and 120,000 or less.

7. A pharmaceutical composition comprising the hyaluronic acid derivative according to claim 1 as a carrier.

8. The pharmaceutical composition according to claim 7, wherein the hyaluronic acid derivative is in the form of a complex with a drug.

9. The pharmaceutical composition according to claim 8, wherein the drug is a protein, a peptide or a nucleic acid having pharmacological activity.

10. A hyaluronic acid derivative-drug complex in which one or more drugs are complexed with the hyaluronic acid derivative according to claim 1.

* * * * *